(12) United States Patent
Radovanovic et al.

(10) Patent No.: US 8,614,095 B2
(45) Date of Patent: Dec. 24, 2013

(54) METHODS FOR IDENTIFYING, PURIFYING AND ENRICHING IMMATURE OR STEM CANCER-INITIATING CELLS FROM TUMORS AND USE THEREOF

(75) Inventors: Ivan Radovanovic, Geneva (CH); Virginie Clement, Ferney-Voltaire (FR)

(73) Assignees: Universite de Geneve, Geneva (CH); Hopitaux Universitaires de Geneve, Geneva (CH)

( * ) Notice: Subject to any disclaimer, the term of this patent is extended or adjusted under 35 U.S.C. 154(b) by 588 days.

(21) Appl. No.: 12/743,979

(22) PCT Filed: Nov. 20, 2008

(86) PCT No.: PCT/IB2008/054872
§ 371 (c)(1),
(2), (4) Date: May 20, 2010

(87) PCT Pub. No.: WO2009/066258
PCT Pub. Date: May 28, 2009

(65) Prior Publication Data
US 2010/0248291 A1 Sep. 30, 2010

Related U.S. Application Data

(60) Provisional application No. 60/996,483, filed on Nov. 20, 2007.

(51) Int. Cl.
*G01N 33/48* (2006.01)
(52) U.S. Cl.
CPC .................................. *G01N 33/48* (2013.01)
USPC .............. 436/63; 435/325; 436/164; 436/176
(58) Field of Classification Search
None
See application file for complete search history.

(56) References Cited

U.S. PATENT DOCUMENTS

| 2006/0148075 A1* | 7/2006 | Feinberg et al. | 435/325 |
| 2009/0104626 A1* | 4/2009 | Kubota et al. | 435/7.1 |
| 2011/0189211 A1* | 8/2011 | Gentry et al. | 424/184.1 |

FOREIGN PATENT DOCUMENTS

WO WO 2005083061 * 9/2005 ............ C12N 5/08

OTHER PUBLICATIONS

Burdsal et al., "Novel Flow-Cytometric Method for Separating Cell Types in Differentiated F9 Embryoid Bodies", Cytometry, vol. 21, No. 2, pp. 145-152 (1995).
Zoli et al., "Flow-Cytometric Determination of Tumor Cells in Lymph Nodes", Oncology, vol. 62, No. 2, pp. 128-135 (Mar. 2002).
Fan et al., "Notch Pathway Inhibition Depletes Stem-like Cells and Blocks Engraftment in Embryonal Brain Tumors", Cancer Research, vol. 66, No. 15, pp. 7445-7452 (Aug. 1, 2006).
Clement et al., "HEDGEHOG-GLI1 Signaling Regulates Human Glioma Growth, Cancer Stem Cell Self-Renewal, and Tumorigenicity", Current Biology, Current Science, vol. 17, No. 2, pp. 165-172 (Jan. 22, 2007).
Maus et al., "Separation of human alveolar macrophages by flow cytometry", American Journal of Physiology, Lung Cellular and Molecuarphysiology, American Physiological Society, vol. 272, No. 3, pp. L566-L571 (Jan. 1, 1997).
McLaren et al., "Analysis of neural stem cells by flow cytometry: cellular differentiation modifies patterns of MHC expression", Journal of Neuroimmunology, vol. 112, No. 1-2, pp. 35-46 (Jan. 1, 2001).
Suvà et al., "Identification of Cancer Stem Cells in Ewing's Sarcoma", Cancer Research, vol. 69, No. 5, pp. 1776-1781 (Mar. 1, 2009).

* cited by examiner

*Primary Examiner* — Gary W Counts
(74) *Attorney, Agent, or Firm* — Hoffmann & Baron, LLP

(57) ABSTRACT

Methods for the preparation of cell compositions based on fluorescence following excitation at wavelength of or about 488 nm and isolated cell compositions obtained therefrom wherein isolated cells exhibit (i) autofluorescence at or about 520 nm or (ii) absence of fluorescence at or about 520 nm and a positive shift in the fluorescence detected at >630 nm. These methods provide for enrichment of immature or stem cancer-initiating cells from tumors (notably, cancers of the central and peripheral nervous system and metastasis to the brain) and methods for screening antitumor agents using the same. Also provided are methods of detecting immature or stem cancer-initiating cells in a cell sample and methods of detecting recurrence of cancer stem cells in a cancer stem cell sample following treatment with an agent.

10 Claims, 20 Drawing Sheets

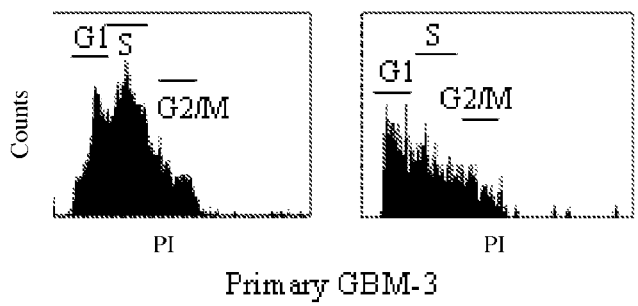
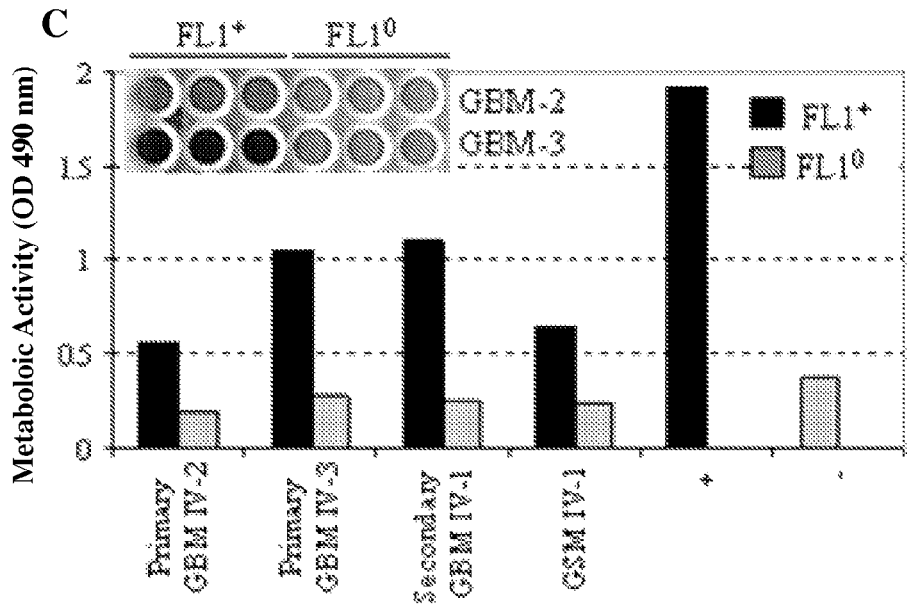
Figure 5

A

| Tumor type | Grade | Location | Gender | Age |
|---|---|---|---|---|
| A II-1 | Astrocytoma grade II | Frontal paramedian left | F | 22 |
| A II-2 | # | nd | M | nd |
| O.G II-1 | Oligodendro-Glioma grade II | Frontal right (SMA) | F | 71 |
| O.A II-1 | Oligodendro-Astrocytoma grade II | Fronto-basal right | F | 44 |
| O.A II-2 | # | nd | M | 41 |
| O.A II-3 | # | Perisylvian caudate | F | 29 |
| O.A II-4 | # | Insular left | M | 35 |
| O.A II-5 | # | Frontal right | F | 44 |
| O.G III-1 | Oligodendro-Glioma grade III | Multifocal insular right | M | 57 |
| O.G III-2 | # | Frontal right | M | 64 |
| O.G III-3 | # |  | F | 37 |
| O.A III-1 | Oligodendro-Astrocytoma grade III | Temporo-amygdala left | M | 52 |
| O.A III-2 | # | Parietal left | F | 45 |
| Primary GBM-1 | GlioBlastoma Multiforme grade IV | Parietal left | M | nd |
| Primary GBM-2 | # | Temporal left | F | 67 |
| Primary GBM-3 | # | nd | nd | nd |
| Primary GBM-4 | # | Occipital right | M | 75 |
| Primary GBM-5 | # | Perisylvian left | M | 52 |
| Primary GBM-6 | # | Frontal left | F | 64 |
| Primary GBM-7 | # | Parietal right | F | 51 |
| Primary GBM-8 | # | Frontal left | F | 48 |
| Primary GBM-9 | # | Frontal right | M | 64 |
| Primary GBM-10 | # | Multifocal | M | 51 |
| Secondary GBM-1 | # | Frontal | M | 64 |
| GSM IV-1 | Gliosarcoma grade IV | Temporal right | M | 70 |

Figure 9

B
| Sphere | % of FL1+ cells | Mean of FL1-II expression |
|---|---|---|
| O.A III-1 | 4.1 | 17.9 |
| Primary GBM-2 | 32 | 341.7 |
| Primary GBM-3 | 44.8 | 476.7 |
| Primary GBM-6 | 59.4 | 381.7 |
| Primary GBM-7 | 5.5 | 69.4 |
| Secondary GBM-1 | 35.8 | 610.0 |
| GSM IV-1 | 26.3 | 43.9 |
Figure 9
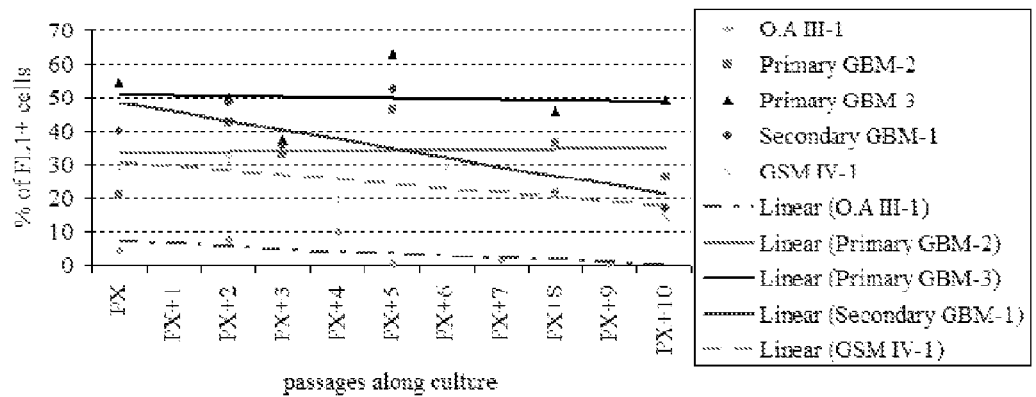
Figure 10
A
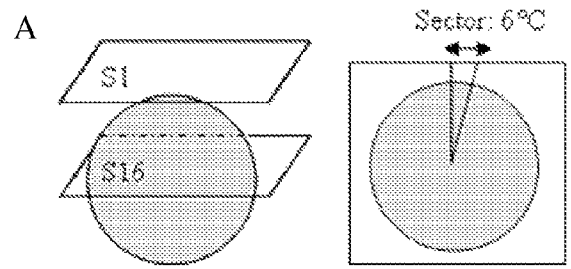
Figure 11

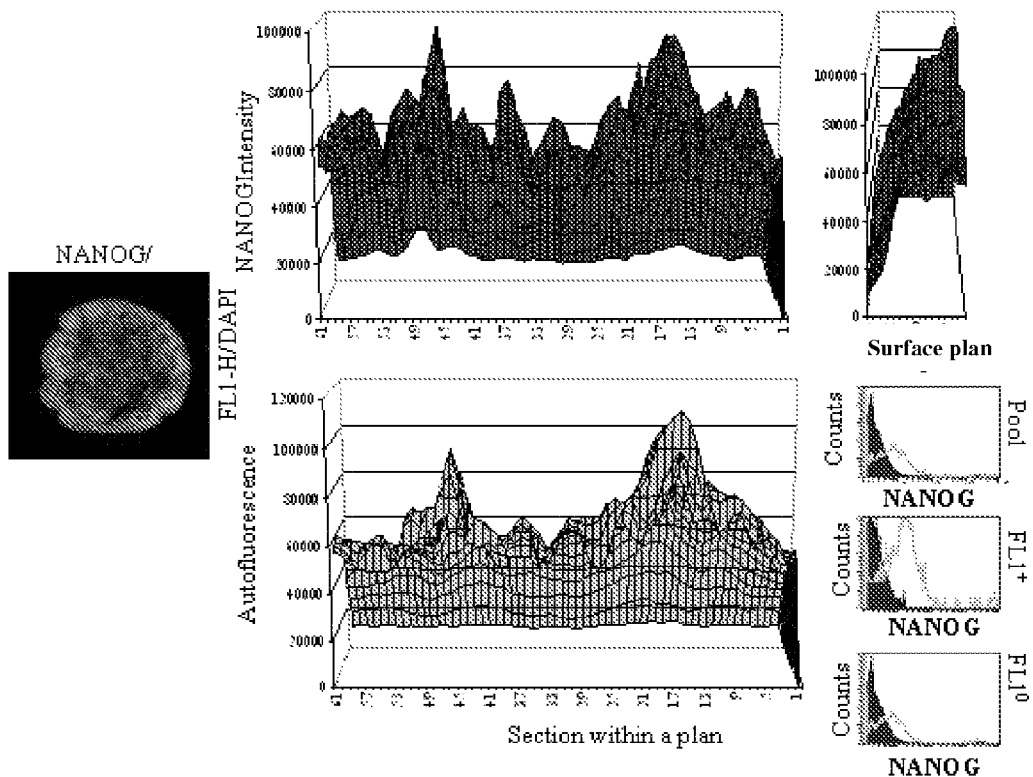
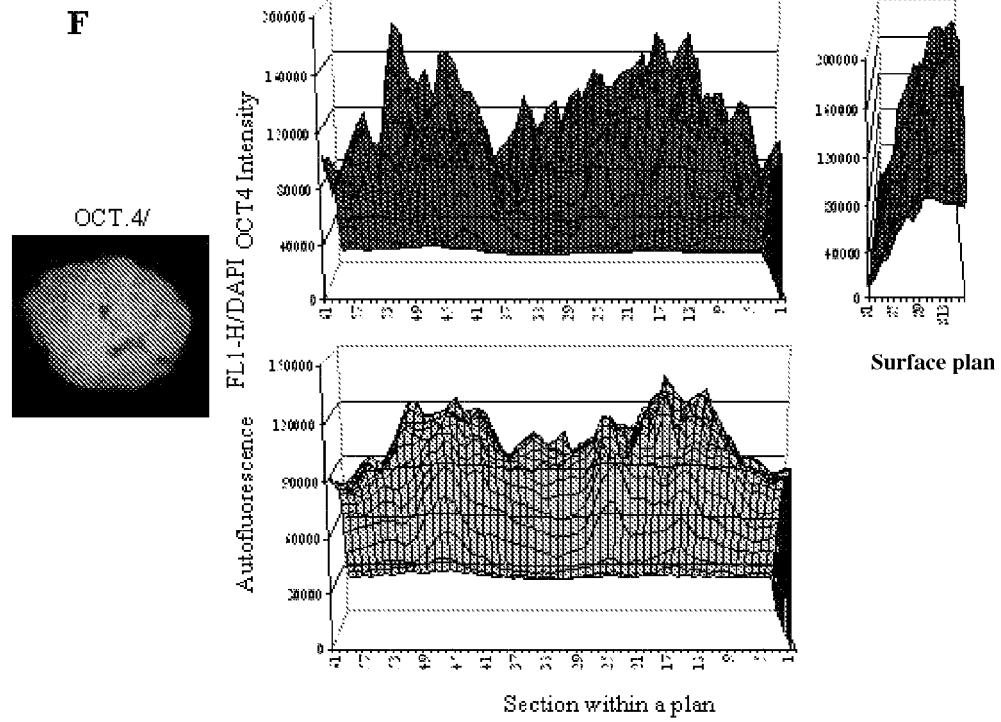
Figure 11

A

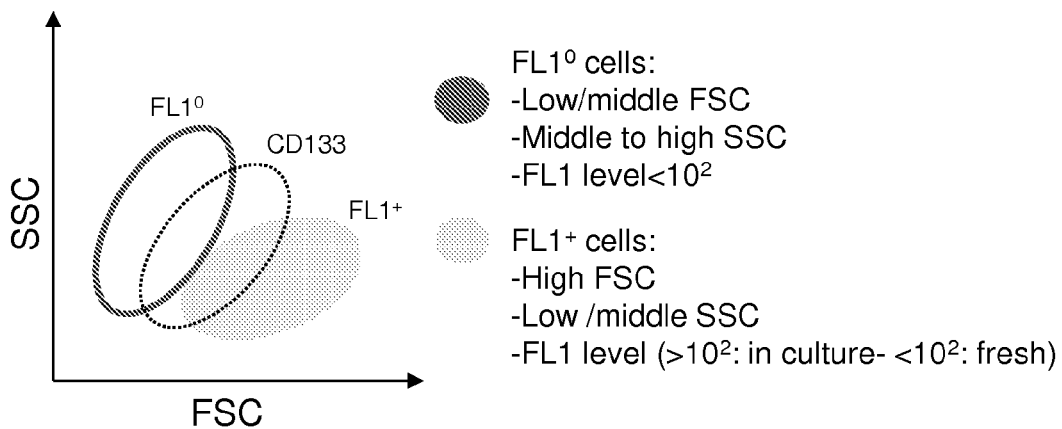

FL1⁰ cells:
-Low/middle FSC
-Middle to high SSC
-FL1 level<$10^2$

FL1⁺ cells:
-High FSC
-Low /middle SSC
-FL1 level (>$10^2$: in culture- <$10^2$: fresh)

B

|  | FL1⁰ | FL1⁺ |
| --- | --- | --- |
| Tumorigenicity | - | + |
| Long term self-renewal | - | + |
| Multipotency | + | + |
| Enrichment for the expression stemness genes (RNAs levels of NANOG, OCT4, SOX2, NOTCH1) | + | +++ |
| Enrichment for the expression of stemness proteins (NANOG, OCT4, SOX2, NOTCH1) | + | + |
| Cell cycle activities (% cells into G2/M phase) | + | +++ |
| Metabolic contents and activities (NADH, LDH content) | + | +++ |

Figure 13

METHODS FOR IDENTIFYING, PURIFYING AND ENRICHING IMMATURE OR STEM CANCER-INITIATING CELLS FROM TUMORS AND USE THEREOF

CROSS-REFERENCE TO RELATED APPLICATIONS

This application is the National Stage of International Application No. PCT/IB2008/054872, which designates the U.S., filed Nov. 20, 2008 which claims the benefit of U.S. Provisional Patent Application No. 60/996,483, filed Nov. 20, 2007, the contents of which are incorporated by reference herein.

FIELD OF THE INVENTION

The present invention relates to methods for the preparation of cell compositions, isolated compositions obtainable therefrom, related isolated cell compositions, kits and use thereof. More specifically, the present invention provides a method for identifying, purifying and enriching immature or stem cancer-initiating cells in a sample. The cell compositions, related methods and uses according to the present invention are useful in the treatment of cancers and/or the detection of enriching immature or stem cancer-initiating cells, notably cancers of the central and peripheral nervous system and metastasis to the brain.

BACKGROUND OF THE INVENTION

Brain tumors-Gliomas are the most frequent brain tumours in adults and, in their malignant form (grade IV or glioblastoma multiforme) remain one of the most aggressive disease with less than 5% of 5-years survival rate (Reardon et al., 2006, *J. Clin. Oncol.*, 24, 1253). Gliomas are classified into subcategories according to their phenotypical resemblance with glial cells, mostly astrocytes (atrocytomas) and oligodendrocytes (oligodendrogliomas). Based on histopathological features, gliomas are also subdivided into low grade (grade I and II) and high grade (grade III and IV) tumors, which have distinct clinical prognosis (Reardon et al., 2006, above). Despite current advances in surgical techniques, as well as radiation and chemotherapeutical strategies, high grade gliomas remain a devastating disease with appalling prognosis. No environmental risk factors have been identified and little is known about the biological mechanisms involved in the initiation and progression phases of these brain tumours. Therefore, any significant improvement in glioma therapy or prophylaxis requests a deeper understanding of cellular and molecular mechanisms of glioma development.

The recent identification of Stem-like Cells (SC) in a number of human cancers like acute myeloid leukemias (AML), breast, ovarian and brain tumors has renewed interest in the hypothesis that cancers may arise from somatic mutations in adult stem/progenitor cells (Reya et al., 2001, *Nature*, 414, 105). A minor population of cancer stem-like cells may represent the source of tumor cell expansion, recurrence and metastasis, thus determining the biological behavior of tumors including proliferation, progression, and subsequently response to therapy (Reya et al., 2001, above; Galmozzi et al., 2006, *Curr. Med. Chem.*, 13, 603). Although normal and cancer stem cells share behavioral similarities including self-renew, differentiation into multiple lineages, they differ regarding their tumorigenic potential when implanted into nude mice (Bonnet and Dick, 1997, *Nat. Med.* 3, 730).

Further, it is exceedingly complex to identify cancer stem marker in human gliomas that are specific for governing tumoral phenotypes. Many efforts are made to find and characterize specific cancer stem cell markers, which would discriminate them from cancer cells (markers of cells from tumor bulk) or from normal stem cells. So far, expression of CD133 was the only possibility to purify and enrich for a subpopulation of glioma stem cells showing self-renewal and tumorigenic properties (Singh et al., 2004, *Nature*, 432, 396). Although CD133 was described in others tumorigenic systems, it is also expressed in normal stem cells, rendering difficult the specific targeting of cancer cells for therapeutics (Yin et al., 1997, *Blood*, 90, 5002; Uchida et al, 2000, *Proc. Natl. Acad. Sci USA*, 97, 14720; Miraglia et al., 1998, *Blood*, 91, 4390). Moreover, it is extremely difficult to believe that only one marker would be sufficient to define "the Glioma Stem Cell Population" knowing the heterogeneity of tumor cell populations, and the current knowledge on the hematopoietic system.

There is therefore a need for new methods allowing a better selection strategy for further understanding of cellular hierarchies in gliomas and other solid cancers, notably new methods to isolate and thoroughly characterize tumor-initiating and -propagating cells showing stem cell properties, which may be useful in the treatment of such cancers.

SUMMARY OF THE INVENTION

The present invention is directed towards methods for the preparation of cell compositions, isolated compositions obtainable therefrom, related isolated cell compositions and use thereof and methods for identifying, purifying and enriching immature or stem cancer-initiating cells in a sample.

A first aspect of the invention provides a method for the preparation of a cell composition according to the invention and isolated compositions obtainable therefrom.

A second aspect of the invention relates to an isolated cell composition comprising living cells which present an autofluorescence emission detected in the FL1 channel upon laser beam excitation are isolated by fluorescence activated cell sorting.

A third aspect of the invention relates to an isolated cell composition comprising living cells which present a slight positive shift in the fluorescence detected in the FL3 and/or FL4 channel by fluorescence activated cell sorting.

A fourth aspect according to the invention resides in a kit comprising at least one cell composition according to the invention.

A fifth aspect according to the invention relates to an use of an isolated cell composition according to the invention in screening methods according to the invention and related methods.

A sixth aspect according to the invention relates to a method of detecting the presence of stem or immature cancer cells in a cell sample.

A seventh aspect according to the invention relates to screening methods for screening antitumor agents for agents able to displace the cells from a tumorigenic state to a non-tumorigenic state.

An eighth aspect according to the invention relates to a method of detecting the recurrence of cancer stem cells in a cancer stem cell sample.

A ninth aspect according to the invention relates to a screening assay comprising or using a cell composition according to the invention.

DESCRIPTION OF THE FIGURES

FIG. 5 shows FL1-H cells, isolated as described in Example 2, enrichment for stemness gene expression and protein levels measured as described in Example 3. (A) Ratio of gene expression levels detected in FL1-H cells over the one of non FL1-H cells. Samples analysed by quantitative real-time PCR and normalized with the geometric mean of GAPDH, TUBG1, and EEF1A expression levels. nd (not determined): in both cases, no gene expression levels were detected in the non-FL1-H cell population. Representative PCR gel pictures of the gene expression levels for the fifth samples showing consistent enrichment in the FL1-H cell population (panel A, left). (B) Cell cycle analysis of $FL1^+$ and $FL1^o$ cells after FACS sorting and Propidium Iodine (PI) staining (left and right panels respectively). The majority of FL1-H cells are in S cell cycle phase whereas the majority of $FL1^o$ cells are in G1 phase. This partially correlates with the absence of metabolic activity detected in $FL1^o$ cells in panel D. (C) Metabolic activity of $FL1^+$ and $FL1^o$ cells after sorting for autofluorescence levels and colorimetric assay (MTS). Values stand for the Optical Density (OD) detected at 490 nm. 293T cells used as positive control whereas media only was used as negative control.

FIG. 9 shows the list of human tissues and their derived gliomasphere cultures (A) List of human gliomas used in this study, classified according to their type and grade. Location, gender and age are documented for each specimen (N=25). (B) Percentage of autofluorescent cells and mean of FL1 intensity in gliomasphere cultures determined by flow cytometry (N=7). A: Astrocytoma; O.G: Oligodendroglioma; O.A: Oligo-astrocytoma; GBM: Glioblastoma multiforme; GSM: Gliosarcoma.

FIG. 10 shows the percentage of the FL1$^+$ population remains stable over >10 passages in various gliomasphere cultures. Although the percentages of FL1$^+$ cells slightly vary from passages to passages, it remains stable over a long period of time in primary GBM-2, -3, secondary GBM-1, and is progressively enriched in O.A III-1 and GSM IV-1 cultures.

FIG. 13 shows how glioma cell populations can be identified and isolated according to a method according to the invention based on their morphology and level of intrinsic fluorescence (at 488 nm excitation wavelength). (A) FL1$^+$ cells harbor a specific morphology and intrinsic fluorescent properties that allows a fast, non-toxic and robust identification, purification, and characterization compared to any other glioma cells within fresh and cultured glioma specimen. (B) Summary of the properties of the FL1$^+$ and FL1$^0$ isolated cells according to the invention.

DETAILED DESCRIPTION

Figure 1:
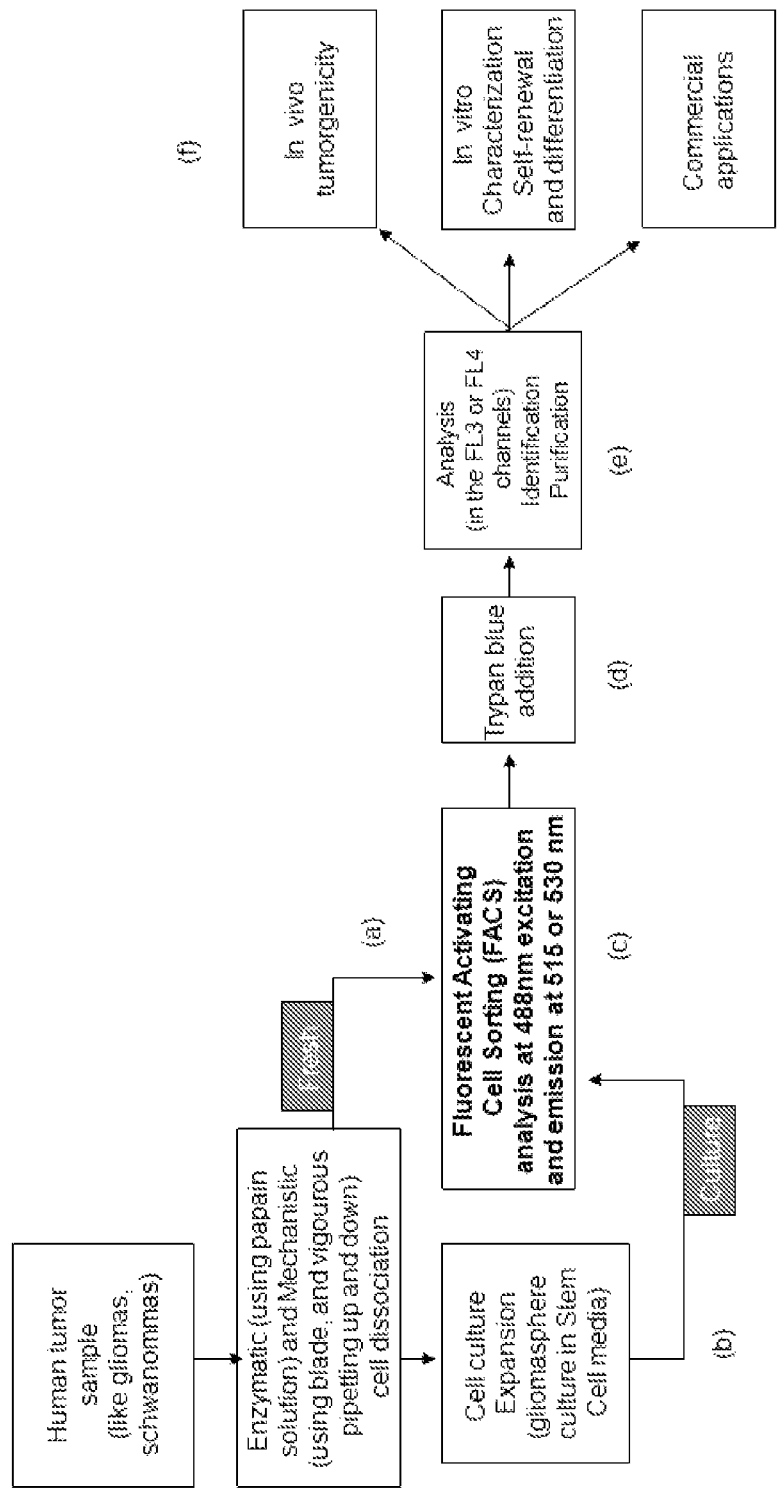
FIG. 1 represents a scheme for a method according to the invention. (a) freshly provided from the tumor cell sample after dissociation. (b) Optionally culturing the cells provided in (a) in a culture medium. (c) Isolating in a sub-sample the cells which present autofluorescence emission detected in the FL1 channel upon laser beam excitation at a wavelength of or about 488 nm by fluorescence activated cell sorting, from the cells provided under step (a) or (b). (d) Isolating in another sub-sample by fluorescence activated cell sorting, the cells which are not fluorescent under step (c) and which present a slight positive shift in the fluorescence detected in the FL3 and/or FL4 channel. (e) Excluding dead cells from each of the isolated cell sub-sample obtained under steps (c) and (d). (f) Pooling the cell sub-sample obtained under step (c) after treatment under step (e). (g) Pooling the cell sub-sample obtained under step (d) after treatment under step (e).

The term "sample" comprises a tissue or fluid sample from any source such as a tissue or fluid sample from a patient (such as a mammalian patient, more specifically a human patient) suffering from a cancer or suspect to suffer from a cancer such as for example human gliomas, schwannomas, metastasis to the brain, meningiomas and ependymomas. In another embodiment, the sample comprises a tissue or fluid sample from any source such as a tissue or fluid sample from a patient (such as a mammalian patient, more specifically a human patient) suffering from a metastatic cancer or suspect to suffer from a cancer such as for example metastasis to the brain from melanoma, breast cancer, colon cancer, lung cancer.

The term "tumor cell sample" comprises cell samples freshly dissociated from a tumor sample or cell samples where the cells have been cultured after dissociation from a tumor sample, like for example gliomasphere cultures such as cultured in stem cell medium and the like, adherent cell cultures such as cultured in serum rich medium and the like and differentiated cell cultures such as cultured in differentiation culture medium and the like.

The term "stem cell medium and the like" includes medium where cancer stem cells (also called gliomaspheres) derived from freshly dissociated tissue sample are expanded. For example, neural stem cell culture medium includes DMEM-F12-Ham's (Gibco) supplemented with Penicillin-streptomycin at 1/1,000 (Gibco), B27 (1/50 Gibco) or BIT9500 (20% Stemcell Technologies), human recombinant EGF (20 ng/ml Invitrogen) and basic FGF-2 (20 ng/ml Invitrogen).

The term "serum rich medium and the like" includes medium where adherent cultures derived from freshly dissociated tissue sample are expanded (e.g. FBS 10%, DMEM-F12-Ham's (Gibco) supplemented with Penicillin-streptomycin at 1/1,000 (Gibco).

The term "differentiation culture medium and the like" includes medium where cancer stem cells are plated for analysing their multipotency capacities (e.g. plates coated with a mixture of poly-Lornithine and Laminin (Sigma) diluted 1:100 in H$_2$O for O/N at 37° C. Cells are dissociated and plated at a density of 10 cell/μl in DMEM-F12-Ham's (Gibco) supplemented with Penicillin-streptomycin at 1/1,000 (Gibco), B27 (1/50 Gibco) or BIT9500 (20% Stemcell Technologies).

The term "expansion medium" defines a medium were cells are expanded in vitro, i.e. where cells grow, divide and give rise to daughter cells by asymmetric or symmetric division.

The term "FL1 channel" is the longitudinal detection channel of fluorescence such as described in *Practical Flow Cytometry*, Shapiro et al., 4$^{th}$ Edition, 2003, Wiley & Sons, Inc. Typically, for an excitation wavelength of 488 nm, the autofluorescence detection occurs in FL1 channel at a wavelength of or about 520 nm.

The term "FL3 channel" is the side detection (45°) channel of fluorescence such as described in *Practical Flow Cytometry*, Shapiro et al., 4$^{th}$ Edition, 2003, Wiley & Sons, Inc. Typically, for an excitation wavelength of 488 nm, the fluorescence detection occurs in FL3 channel at a wavelength >630 nm.

The term "FL4 channel" is the side detection channel of fluorescence such as described in *Practical Flow Cytometry*, Shapiro et al, 4th Edition, 2003, Wiley & Sons, Inc. Typically, for an excitation wavelength of or about 632 nm or of or about 546 nm, the fluorescence detection occurs in FL4 channel at a wavelength >630 nm.

The term "cancer" comprises cancers such a cancers of the central and peripheral nervous system, metastasis to the brain and lung metastasis, acute myeloid leukemias (AML), breast and ovarian tumors. Further, the term cancer comprises cancers such as melanoma, breast cancer, colon cancer.

The term "FL1$^+$ cells" or "FL1-H cells" refers to cells that are sorted by fluorescence activating cell sorting through a method according to the invention, notably by selectively detecting and sorting cells which present a specific morphology (high FSC and low/middle SSC) and autofluorescence emission detected in the FL1 channel upon laser beam excitation into a cell sub-sample. This sub-sample consists in a cell sub-population presenting such autofluorescence emission detected in the FL1 channel is detected upon excitation at a wavelength of 488 nm (for example a blue laser beam, e.g. Argon) at a wavelength around 520 nm. More specifically, the FL1 autofluorescence can be detected in the FL1 channel with a dichroïc mirror at 530 nm+/−15, and more tightly with a dichroïc mirror at 515 nm+/−5, confirming the specificity of the FL1 autofluorescence emission spectrum.

The term "FL1$^0$ cells" or "non FL1-H cells" or "non-autofluorescent cells" refers to cells that are sorted by fluorescence activating cell sorting through a method according to the invention, notably by selectively detecting and sorting cells which present a specific morphology (low/middle FSC and middle/high SSC), are not fluorescent in the FL1 channel and present a slight positive shift in the fluorescence detected in the FL3 or FL4 channel.

The term "high FSC" or "high FSC-H" or "high FSC-A" means Forward Scatter and corresponds to the particle (cell?) size and velocity measuring (cell diameter between 5-7 μm).

The term "low/middle FSC" or "low/middle FSC-H" or "low/middle FSC-A" means Forward Size Scatter and corresponds to the size of the cell (cell diameter <5-7 μm).

The term "middle/high SSC" or "middle/high SSC-H" or "middle/high SSC-A" means Side or Orthogonal Scatter and corresponds to cell complexity or granularity (cells with large cytoplasm and granular).

The term "low/middle SSC" or "low/middle SSC-H" or "low/middle SSC-A" means Side or Orthogonal Scatter and corresponds to cell complexity or granularity (cells with agranular and confined cytoplasm around nucleus).

Typically, FL1$^+$ or FL1-H cells combined a "high FSC" or "high FSC-H" or "high FSC-A" with "low/middle SSC" or "low/middle SSC-H" or "low/middle SSC-A", and have therefore a nuclear/cytoplasmic diameter ratio >1.

Typically, FL10 or non-FL1-H cells combined a "low/middle FSC" or "low/middle FSC-H" or "low/middle FSC-A" with "middle/high SSC" or "middle/high SSC-H" or "middle/high SSC-A", and have therefore a nuclear/cytoplasmic ratio <1.

The term "cancer stem cell sample" means an isolated cell composition according to the invention or a cell composition obtainable by a method for the preparation of a cell composition according to the invention.

The term "stem cell culture medium" is a medium suitable for the culture of stem cells. Typically, a stem cell culture medium includes for example mitogenes (bFGF, EGF) and supplement free-media (B27 or BIT9500).

The term "spherogenicity" comprises the capacity of a single stem cell to divide symmetrically or asymmetrically to form a clone. This clone is called sphere, and more precisely, it is called a gliomasphere when the sphere derived from a glioma tumor. This capacity can be measured by clonal assay also called self-renewal assay such as described in Example 3 and on FIG. 2. Self-renewal assay does measure the ability of a single cell to form a clone, but not all clones do form sphere. Only stem cell or early progenitor in normal development or certain cancer type shows this spherogenic potential, and this specificity exist in neural and glioma stem cells.

The term "multipotency" comprises the capacity of the cells to differentiate into several cell types, e.g. for cells from the central nervous system mutipotency refers to the capacity to differentiate into cells such as GFAP (astrocytes), NESTIN (neural progenitors), TUJ1 (neurons).

The term "recovery" comprises the transfer of FL1$^+$ and FL1$^0$ cells back into the stem cell media after treatment. The term "antitumor agent" comprises molecules susceptible to have a therapeutic activity in a cancer, e.g. effective in the treatment of a cancer such as in decreasing or abolishing tumour growth, in preventing, decreasing or abolishing the cancer recurrence. It comprises agents that are known for their therapeutic activity in a cancer or agents which are investigated for their ability to have a therapeutic activity in a cancer. The term "recurrence" means the ability of a cancer stem cell to survive, to maintain its intrinsic properties (e.g. autofluorescence in FL1 channel, spherogenicity), its division ability and optionally to maintain further properties (e.g. differentiation ability as measured by expression of differentiation markers, stemness properties as measured by expression of stemness markers and metabolic properties such as measured by the activity and ratio NAD/NADPH+ enzymes using an oxido-reduction colorimetric assay (MTS)) after treatment by an agent. Measurement of recurrence is performed by a screening assay according to the invention and comprises the analyses of the presence and proportion of FL1$^+$ and FL1$^0$ cells after the treatment such as summarized on FIG. 14. The recurrence level will be evaluated on the basis of the proportion of surviving cancer stem cells after treatment during the recovery period and on the length of the recovery period during which no recurrence of cancer stem cells is observed.

The term "ability to inhibit cancer stem cells recurrence" refers to the property of an agent which is able to decrease the number of cancer stem cells in a cancer stem cell sample after treatment and after observation of a recovery period after this treatment. Preferably, the ability to inhibit cancer stem cells recurrence is the ability of an agent to eliminate cancer stem cells from a cancer stem cell sample and to avoid the recurrence of those cells after the observation of a recovery period.

The term "agent" includes any molecules (e.g. chemical, biological) or any external/environmental factor (e.g. mechanical, radiation).

The term "cancer stem cell sample" means a sample selected from a gliomasphere culture (cultured as described in the examples) containing a mixture of FL1$^+$ and FL1$^0$ cells according to the invention or a sample containing two isolated FL1$^+$ or FL1$^0$ cell populations wherein cells are isolated by a method according to the invention.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or relieving the disease, i.e., causing regression of the disease and/or its symptoms or conditions.

The term "inhibitor" used in the context of the invention is defined as a molecule that completely or partially the activity of biological molecule.

The term "isolated" is used to indicate that the cell is free of association with other cells, proteins or polypeptides, for example as a purification product or as a purified extract.

The term "subject" as used herein refers to mammals. For examples, mammals contemplated by the present invention include human, primates, domesticated animals such as cattle, sheep, pigs, horses and the like.

In one embodiment according to the invention, is provided a method for the preparation of a cell composition, comprising the steps of:

(a) Providing a tumor cell sample;
(b) Optionally culturing the cells provided in (a) in a culture medium;
(c) Isolating in a sub-sample the cells which present autofluorescence emission detected in the FL1 channel upon laser beam excitation at a wavelength of or about 488 nm by fluorescence activated cell sorting, from the cells provided under step (a) or (b);
(d) Isolating in another sub-sample by fluorescence activated cell sorting, the cells which are not fluorescent under step (c) and which present a slight positive shift in the fluorescence detected in the FL3 and/or FL4 channel;
(e) Excluding dead cells from each of the isolated cell sub-sample obtained under steps (c) and (d);
(f) Pooling the cell sub-sample obtained under step (c) after treatment under step (e);
(g) Pooling the cell sub-sample obtained under step (d) after treatment under step (e).

In a further embodiment, the invention provides a method according to the invention wherein the cells isolated under step (c) are those which further present a specific morphology (high FSC and low/middle SSC) under fluorescence activated cell sorting.

In a further embodiment, the invention provides a method according to the invention wherein the cells isolated under step (d) are those which further present a specific morphology (low/middle FSC and middle/high SSC) under fluorescence activated cell sorting.

In a further embodiment, the invention provides a method according to the invention wherein the autofluorescence emission detected under step (c) is detected in the FL1 channel, at a wavelength of or about 520 nm.

In another further embodiment, the invention provides a method according to the invention wherein the autofluorescence emission detected under step (c) detected in the FL1 channel with a dichroïc mirror at 530 nm+/−15 nm.

In another further embodiment, the invention provides a method according to the invention wherein the autofluorescence emission detected under step (c) detected in the FL1 channel with a dichroïc mirror at 515 nm+/−5 nm.

In another further embodiment, the invention provides a method according to the invention wherein the slight positive shift in the fluorescence emission detected under step (d) is detected at a wavelength >630 nm.

In another further embodiment, the invention provides a method according to the invention wherein dead cells are excluded under step (e) by trypan blue addition to the sub-samples obtained under steps (c) and (d).

In another further embodiment, the invention provides a method according to the invention wherein the tumor cell sample provided under step (a) is a sample wherein the cells have been cultured after dissociation from a tumor sample.

In another further embodiment, the invention provides a method according to the invention wherein the tumor cell sample provided under step (a) is a freshly dissociated from a tumor sample.

In another further embodiment, the invention provides a method according to the invention wherein the culture medium under step (b) is selected from a stem cell medium, a serum rich medium and a differentiation culture medium.

In another further embodiment, the invention provides a method according to the invention wherein the tumor cell sample provided under step (a) is a sample where cells have been dissociated from a tumor sample selected from gliomas, schwannomas, metastasis to the brain, meningiomas and ependymomas.

In another further embodiment, the invention provides a method according to the invention wherein the tumor cell sample provided under step (a) is a sample where cells have been dissociated from a tumor sample selected from a metastasis to the brain from melanoma, breast cancer, colon cancer, lung cancer.

In another embodiment, the invention provides an isolated cell composition comprising living cells which present an autofluorescence emission detected in the FL1 channel upon laser beam excitation at or about 488 nm by fluorescence activated cell sorting.

In another further embodiment, the invention provides an isolated cell composition comprising living cells which present a specific morphology (high FSC and low/middle SSC) and an autofluorescence emission detected in the FL1 channel upon laser beam excitation at or about 488 nm by fluorescence activated cell sorting.

In another embodiment, the invention provides an isolated cell composition comprising living cells which do not present an autofluorescence emission detected in the FL1 channel upon laser beam excitation at or about 488 nm and present a slight positive shift in the fluorescence detected in the FL3 and/or FL4 channel by fluorescence activated cell sorting.

In another further embodiment, the invention provides an isolated cell composition comprising living cells which do not present a specific morphology (high FSC and low/middle SSC), nor an autofluorescence emission detected in the FL1 channel upon laser beam excitation at or about 488 nm but present a specific morphology (low/middle FSC and middle/high SSC), a slight positive shift in the fluorescence detected in the FL3 and/or FL4 channel by fluorescence activated cell sorting.

In another embodiment, the invention provides an isolated cell composition comprising a cell sub-sample obtainable by a method according to the invention.

In a further embodiment, the invention provides an isolated cell composition according to the invention wherein the cell sub-sample is obtained under step (f).

In another further embodiment, the invention provides an isolated cell composition according to the invention, wherein the cell sub-sample is obtained under step (g).

In another further embodiment, the invention provides an isolated cell composition according to the invention, wherein the cells are glioma cells.

In another embodiment, the invention provides a kit comprising at least on cell composition according to the invention.

In another embodiment, the invention provides a screening method for screening for antitumor agents comprising the following steps:

(i) Combining an isolated cell composition according to the invention (FL1$^+$ cells), in presence/absence of an agent to be screened;
(ii) Determining the ability of the agent to inhibit at least one FL1$^+$ cell function.

In a further embodiment, the invention provides a screening method for screening for antitumor agents according to the invention wherein step (ii) comprises determining the ability of the agent to inhibit FL1$^+$ cell function by measuring self-renewal, tumorigenicity, and enrichment for stemness gene properties, cell cycle and metabolic functions.

In another embodiment, the invention provides a method of detecting the presence of stem or immature cancer cells in a cell sample, comprising the following steps:
(a) Providing a cell sample;
(b) Optionally culturing the cells provided in (a) in a culture medium;
(c) Detecting cells by fluorescence activated cell sorting cell which present autofluorescence emission in the FL1 channel upon laser beam excitation at a wavelength of or about 488 nm from cells provided under step (a) or (b);
(d) Detecting cells by fluorescence activated cell sorting which do not present autofluorescence emission in the FL1 channel under step (c) and present a slight positive shift in the cell fluorescence emission in the FL3 and/or FL4 channel upon laser beam excitation of cells provided under step (a) or (b);
(e) Determining the ratio of fluorescence signals obtained under step (d) and obtained under step (c).

In another embodiment, the invention provides a method of detecting the presence of stem or immature cancer cells in a cell sample wherein the cells detected under step (c) are those which further present a specific morphology (high FSC and low/middle SSC) under fluorescence activated cell sorting.

In another embodiment, the invention provides a method of detecting the presence of stem or immature cancer cells in a cell sample wherein the cells detected under step (d) further present a specific morphology (low/middle FSC and middle/high SSC) under fluorescence activated cell sorting.

In another embodiment, the invention provides a method of detecting the presence of stem or immature cancer cells in a cell sample wherein the method further comprises a step (f) after step (c) of calculating the percentage of cells detected under step (c) within the sample.

In a further embodiment, the invention provides a method of detecting the presence of stem or immature cancer cells in a cell sample wherein the method further comprises, after step (f), a step (g) of comparing the calculated percentage under step (f) to a standard percentage (e.g. from or about 0.1% to or about 6%).

In another further embodiment, the invention provides a method of detecting the presence of stem or immature cancer cells in a cell sample wherein the method further comprises, after step (d), a step (h) of isolating in separate samples (FL1$^+$ and FL1$^0$) cells detected under step (d) and/or under step (c).

In another further embodiment, the invention provides a method of detecting the presence of stem or immature cancer cells in a cell sample wherein the method further comprises, after step (h), a step (j) of selecting the viable cell population from cell samples isolated under step (h).

In another further embodiment, the invention provides a method of detecting the presence of stem or immature cancer cells in a cell sample wherein the method further comprises, after step (j), a step (k) of characterizing at least one property of the cells provided under step (j), wherein the properties are selected from stem properties, tumorigenicity, integration, self-renewal and multipotency.

In another further embodiment, the invention provides a method of detecting the presence of stem or immature cancer cells in a cell sample wherein the method further comprises, after step (j), a step (k) of determining the expression of at least one differentiation marker (e.g. by immunochemistry or by FACS staining TUJ1, MAP2 or GFAP) on the cell samples provided under step (j).

In another further embodiment, the invention provides a method of detecting the presence of stem or immature cancer cells in a cell sample wherein the method further comprises, after step (j), a step (k') of determining the expression of at least one stemness marker (e.g. by qRT-PCT using NANOG, OCT4, SOX2, NOTCH1 genes) on the cell samples provided under step (j).

In another further embodiment, the invention provides a method of detecting the presence of stem or immature cancer cells in a cell sample wherein the method further comprises, after step (j), a step (k') of determining the percentage of dividing cells on the cell samples provided under step (j) (e.g. by FACS cell cycle analysis with propidium iodide, immunochemistry or FACS staining with an anti-Ki67 antibody).

In another embodiment, the invention provides a method of detecting the recurrence of cancer stem cells in a cancer stem cell sample, comprising the following steps:
(a) Providing a cancer stem cell sample;
(b) Treating the cancer stem cell sample provided under (a) with an agent;
(c) Incubating the treated stem cell sample in a stem cell culture medium for an incubation period without treatment;
(d) Selecting the viable cell population from the stem cell sample incubated under step (c);
(e) Measuring the mean level of autofluorescence on the viable cell population isolated under step (d) by detecting, by fluorescence activated cell sorting, cells presenting autofluorescence emission in the FL1 channel upon laser beam excitation at a wavelength of or about 488 nm;
(f) Isolating cells by fluorescence activated cell sorting cell which have a specific morphology (high FSC and low/middle SSC) and present autofluorescence emission in the FL1 channel upon laser beam excitation at a wavelength of or about 488 nm of the viable cell population isolated under step (d);
(g) Isolating cells by fluorescence activated cell sorting which have a specific morphology (low/middle FSC and middle/high SSC), do not present autofluorescence emission in the FL1 channel under step (d) and present a slight positive shift in the cell fluorescence emission in the FL3 and/or FL4 channel upon laser beam excitation of the viable cell population isolated under step (d);
(h) Calculating the percentage of autofluorescent viable cells by comparing the mean level of autofluorescence in the cancer stem cell sample provided under step (a) and the mean level of autofluorescence measured under step (e);
(i) Calculating the percentage of the cell death by comparing the number of initial cells present in the cancer stem cell sample provided under step (a) and the resulting viable cell population isolated under step (d);
(j) Calculating the percentage of viable FL1$^+$ cells by comparing the number of initial FL1$^+$ cells present in the cancer stem cell sample provided under step (a) and the resulting viable FL1$^+$ cell population isolated under step (f);
(k) Calculating the percentage of viable FL1$^0$ cells by comparing the number of initial FL1$^0$ cells present in the cancer stem cell sample provided under step (a) and the resulting viable FL1$^0$ cell population isolated under step (g);

(l) Detecting spherogenicity of the cell populations detected under steps (f) and (g).

(m) Determining the activity of the agent through its ability to inhibit cancer stem cells recurrence.

In another further embodiment, the invention provides a method of detecting the recurrence of cancer stem cells in a cancer stem cell sample wherein the method further comprises, after step (l), a step (l1) of determining the expression of at least one differentiation marker (e.g. by immunochemistry or by FACS staining TUJ1, MAP2 or GFAP) on the cell populations detected under steps (f) and (g).

In another further embodiment, the invention provides a method of detecting the recurrence of cancer stem cells in a cancer stem cell sample wherein the method further comprises, after step (l), a step (l2) of determining the expression of at least one stemness marker (e.g. by qRT-PCT using NANOG, OCT4, SOX2, NOTCH1 genes) on the cell populations detected under steps (f) and (g).

In another further embodiment, the invention provides a method of detecting the recurrence of cancer stem cells in a cancer stem cell sample wherein the method further comprises, after step (l), a step (l3) of determining the percentage of dividing cells on the cell populations detected under steps (f) and (g) (e.g. by FACS cell cycle analysis with propidium iodide, immunochemistry or FACS staining with an anti-Ki67 antibody).

In another further embodiment, the invention provides a method of detecting the recurrence of cancer stem cells in a cancer stem cell sample wherein the method further comprises, after step (l), a step (l4) of determining the metabolic activity of $FL1^+$ and $FL1^0$ cells.

In another further embodiment, the invention provides a method of detecting the recurrence of cancer stem cells in a cancer stem cell sample wherein the method further comprises, after step (l), a step (l4) of determining the NADH and LDH contents and activities on the cell populations detected under steps (f) and (g) (e.g. by colorimetric assay).

In a particular aspect according to the invention, the tumor cell sample is a mammalian tumor cell sample.

In a further embodiment, the tumor cell sample is a human tumor cell sample.

In a further embodiment, the invention relates to a screening assay comprising or using an isolated cell composition according to the invention.

General Procedures & Conditions

The method according to the invention is a non-toxic and direct method for identifying, purifying and enriching immature or stem cancer-initiating cells from a cell sample (e.g. cells dissociated from tumors like gliomas, tumors derived from the peripheral nervous system (schwannomas), metastasis to the brain, meningiomas and ependymomas, which may be exemplified schematically as presented on FIG. 1.

For the preparation of a tumor cell sample (for example from human source) for use in a method according to the invention under step (a) and a composition according to the invention, the cells are prepared according to the general protocol as follows:

(A) Biopsy

A biopsy of the corresponding tumor tissue is obtained under sterile conditions using standards methods adapted to the specific cells that will be collected. Example of tumor samples used are listed under FIG. 9A.

(B) Cell Dissociation

Cells then are dissociated from the tumor tissue obtained from the biopsy (A) using standards methods such as enzymatic methods (e.g. papain solution) and/or by mechanistic standards methods (e.g. blade and vigorous pipetting up and down) combined with appropriate incubation, washing, antibiotic supplementation and centrifugation steps as described in standard methods.

The freshly dissociated cells obtained are then used as a tumor cell sample either (FIG. 1(a)) extemporaneously or (FIG. 1(b)) after ex-vivo culture and cell proliferation as follows.

Ex-Vivo Culture and Cell Proliferation (Method According to the Invention Step (b))

Cells used as a tumor cell sample in the context of the invention may be cultured in different media such as such as in a stem cell medium and the like, in a serum rich medium and the like or in a differentiation culture medium and the like. The culture medium may be adapted by the person skilled in the art, depending on the type of tumour cell to be cultured. The cell culture step comprises a combination of appropriate incubation, washing, antibiotic and growth factors or mitotic agent supplementation and centrifugation steps as described in standard methods. These steps are repeated until spheres (gliomasphere in the case where the sphere is derived from a glioma tumour) appears. The appearance of spheres may be assayed by clonal assay (also called self-renewal assay) as described in Example 3 below and on FIG. 2. Once cells are starting to form spheres, the cells are dissociated (e.g. mechanistically) from the cell culture medium.

Cell Sorting by Fluorescence Activated Cell Sorter (FACS) (Method According to the Invention Steps (c) & (d))

Cell are sorted by fluorescence activating cell sorting by selectively detecting and sorting cells which present autofluorescence emission detected in the FL1 channel upon laser beam excitation into a cell sub-sample. This sub-sample consists in a cell sub-population presenting such autofluorescence emission detected in the FL1 channel (also called $FL1^+$) is detected upon excitation at a wavelength of 488 nm (for example a blue laser beam, e.g. Argon) at a wavelength around 520 nm. More specifically, the FL1 autofluorescence can be detected in the FL1 channel with a dichroïc minor at 530 nm+/−15, and more tightly with a dichroïc minor at 515 nm+/−5, confirming the specificity of the FL1 autofluorescence emission spectrum. The cells having a specific morphology (high FSC and low/middle SSC) are further selected.

Non-autofluorescent cells (also called $FL1^0$) are sorted by fluorescence activating cell sorting by selectively detecting and sorting cells which are not fluorescent in the FL1 channel and present a slight positive shift in the fluorescence detected in the FL3 or FL4 channel (step (e)) into another cell sub-sample. The cells having a specific morphology (low/middle FSC and middle/high SSC) are further selected.

Exclusion of Dead Cells from the Cell Preparation (Method According to the Invention Step (e))

The dead cells are excluded from the identified and isolated $FL1^+$ and $FL1^0$ sub-populations, for example by trypan blue addition, thereby contributing to amplify the detection of $FL1^0$ sub-population and achieving the discrimination between the 3 cell populations (dead cells, $FL1^0$ and $FL1^+$). The isolated $FL1^+$ cells display in vitro stemness properties such as multipotency and self-renewal by symmetric and asymmetric division, spherogenic potential, selective tumorigenicity and can propagate tumor growth in vivo as shown in the examples below. Furthermore, $FL1^+$ autofluorescent cell population, which preferentially expresses stemness related genes, has enhanced metabolic activity.

Uses of the Discriminated Obtained Cell Populations

The isolated sub-populations ($FL1^0$ and $FL1^+$) obtained by the method according to the invention may be used for different purposes.

Figure 2:
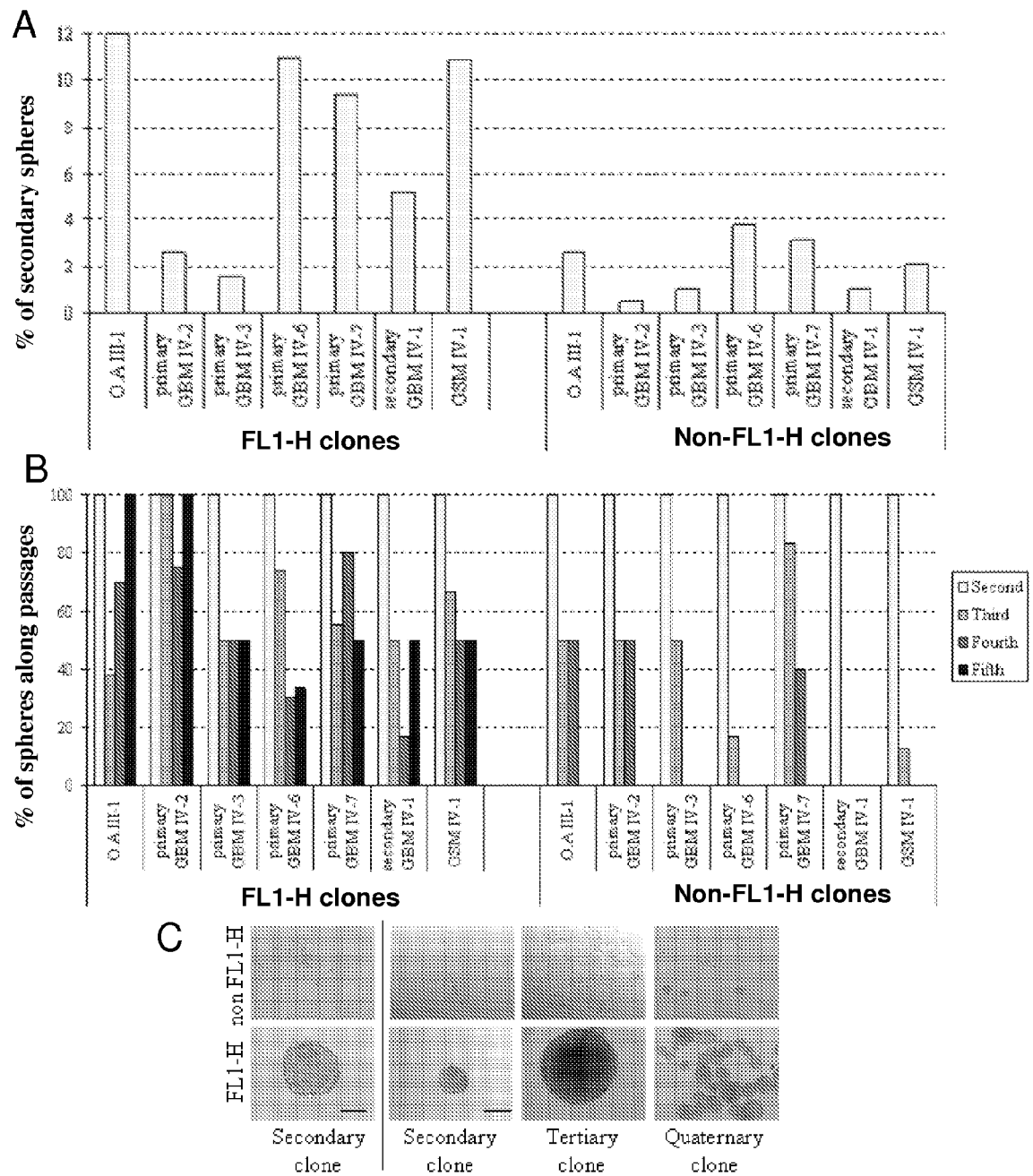
FIG. 2 shows that $FL1^+$ cells have a higher spherogenic properties than $FL1^o$ cells, and exclusively long-term self-renewal ability. (A) Percentage of secondary sphere units formed after $FL1^+$ and $FL1^o$ sorting, and cloning at 1 cell/well. Sphere counting assessed at 10 days post-cloning. (B) Serial passages (up to fifth) of individual clones derived from one single $FL1^+$ or from one single $FL1^o$ cell. While the FL1 positive clones can be passed more than 5 passages, the majority of the $FL1^o$ clones do not form spheres after 4 passages any more. (C) Phase-contrast images of two individual clones along serial passages. Left panel: morphology of the $FL1^+$ and $FL1^o$ clones. While the $FL1^+$ clone is a sphere, the $FL1^o$ clone consists of attached cells although both clones were cultured in stem cell conditions. Right panel: pictures at lower magnification of the evolution and growth of both $FL1^+$ and $FL1^o$ individual clones up to passage 4. Tumor sample type legends are on FIG. 9A.

For example, an isolated cell composition according to the invention may be used in a screening method for screening antitumor agents (e.g. chemicals, drugs or any biological compounds and the like) comprising the following steps:
(i) Combining a cell composition according to the invention (FL1$^+$ cells), in presence/absence of an agent to be screened;
(ii) Determining the ability of the agent to inhibit at least one FL1$^+$ cell properties and functions (e.g. self-renewal, viability, tumorigenicity). For example by measuring FL1$^+$ cell percentage, the metabolic activity of FL1$^+$ cells, the cell cycle and viability, by testing their ability to form secondary spheres (FIGS. 2 and 13).

For example, an isolated cell composition according to the invention may be used to identify tumorigenic genes, and anti-tumor gene targets by profiling (differential expression levels of proteins and mRNAs, RNA, protein) or to identify specific peptides for generating antibodies, vaccines, (pulsed dendritic cells) for immunotherapy strategy.

For example, an isolated cell composition according to the invention may be used to identify and develop new medium complements to improve culture conditions for expanding cell cultures from low grade gliomas (Grade II, III).

For example, an isolated cell composition according to the invention may be used to identify the existence or presence of an autofluorescent FL1$^+$ in normal context. This means to use the technique described above to isolate and characterize normal stem cells in order to develop drugs for tissue repair, stem cell re-population, tracing, viability of stem cells in vivo.

The method according to the invention for identifying, purifying and enriching immature or stem cancer-initiating cells from a cell sample (e.g. cells dissociated from tumors like gliomas, tumors derived from the peripheral nervous system schwannomas), metastasis to the brain, meningiomas and ependymomas) may be used to identify and define the immature/stem cancer cell ratio using fluorescent activating cell sorting (FACS). This method allows analysis of cells with a high level of autofluorescence FL1$^+$ (mean >10$^1$) or a low level of autofluorescence FL1$^0$ (mean <10$^1$).

This method may be used to detect the presence of stem or immature cancer cells in a cell sample for example for diagnostics.

Typically, in an aspect of the invention is provided a method according to the invention wherein the cell sample provided under step (a) is a sample from a patient suffering from a cancer or suspect to suffer from a cancer such as for example human gliomas, schwannomas, metastasis to the brain, meningiomas and ependymomas. Further, in another aspect of the invention, is provided a method according to the invention wherein the cell sample provided under step (a) is a sample from a patient suffering from a metastatic cancer or suspect to suffer from a cancer such as for example metastasis to the brain from melanoma, breast cancer, colon cancer, lung cancer.

According to one aspect, the method of the invention may further comprise a step of comparing the calculated percentage of cells detected by autofluorescence by FACS in the FL1 channel upon laser excitation to a standard percentage. Typically, this standard percentage is a cell percentage calculated by the same method on a cell sample from an healthy patient or a cell sample of the same patient measured earlier (e.g. before surgery, before treatment, right after surgery, right after treatment etc. . . . ).

Once those FL1$^+$ cells are detected, specific local resection or treatment of the tumor in vivo may be prescribed.

In the absence of specific and reliable stem markers and because of the complexity of sorting by entire patterns or "signatures" it might be more appropriate to use indirect means such as morphological characteristic or properties that reflect or are reasonably correlated to an increased stemness state. Therefore, it is useful reconsidering the criteria for glioma initiating cells detection and using a selection strategy according to the invention based not on predetermined molecular markers but on general, robust and easily detectable cellular characteristics such as shown on FIG. 13 (autofluorescence, particular morphology or metabolic state). Furthermore combination of an easy non molecular first sorting step with different molecular markers might in the future refine glioma stem cell isolation.

Examples illustrating the invention will be described hereinafter in a more detailed manner and by reference to the embodiments represented in the Figures. References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

EXAMPLES

The following abbreviations refer respectively to the definitions below: mg (milligram), ml (milliliter), mM (millimolar), mM (minute), ng (nanogram), nm (nanometer), rpm (rotation per minute), AML (acute myeloid leukemia), CM (conditioned media), EGF (Epidermal Growth Factor), DMEM (Dulbecco's Modified Eagle Medium), EDTA (ethylenediaminetetraacetic acid), FACS (Fluorescence Activated Cell Sorter), FBS (Fetal Bovine Serum), FSC (Forward scatter), FGF-2 (fibroblast growth factor 2), LDH (Lactate dehydrogenase), MHCl (major histocompatibility complex I), MRI (Magnetic Resonance Imaging), MTS ([3-(4,5-dimethyl-2-yl)-5-(3-carboxymethoxyphenyl)-2-(4-sulfophenyl)-2H-tetrazolium, inner salt); NADH (nicotinamide adenine dinucleotide), PBS (Phosphate Buffered Saline), PES (phenazine ethosulfate), PCNA (Proliferating Cell Nuclear Antigen), PI (Propidium Iodine), SC (Stem Cell), SSC (Side scatter).

Example 1

Figure 3:
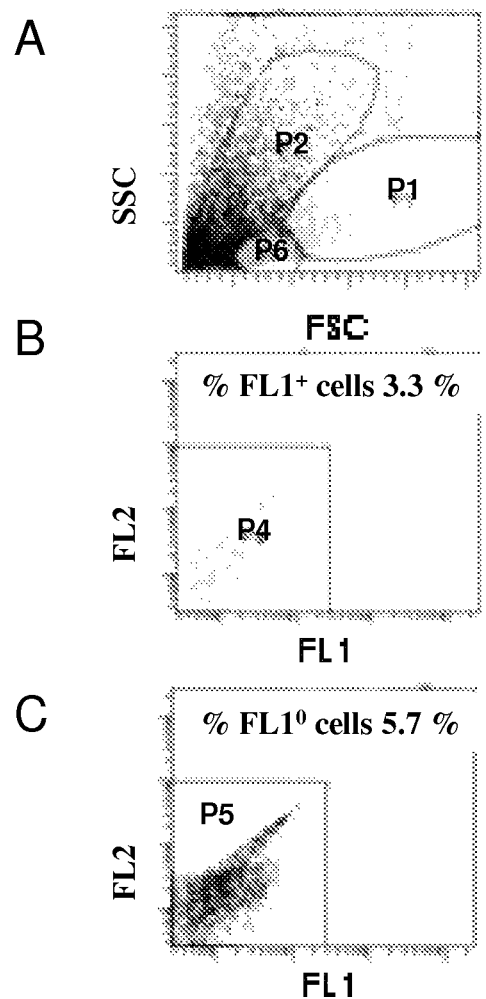
FIG. 3 shows a cell analysis performed on a fresh specimen as described in Example 1 (A): entire population, (B): $FL1^+$; C: $FL1^o$. Autofluorescence emits specifically in the FL1 channel (515+/−5 nm or 530+/−15 nm). Light gray dots gate viable $FL1^+$ cells with a low SSC, and high FCS profiles (P1). Dark gray gate viable $FL1^o$ cells with a different morphology (low/middle SSC and FSC profiles; P2). P4 and P5 gate $FL1^+$ and $FL1^o$ cells respectively with low levels of fluorescence ($<10^2$). P6 represents a small population with low SSC and FSC, which is only detected in fresh primary human sample or in tissue from mice bearing tumors. Black dots represent the broad non-gated population which does not stand any other criteria, and includes dead cells.

Method for Analyzing and Purifying Freshly Dissociated Cancer-Initiating Cells (FIG. 3)

The method according to the invention is performed on a freshly dissociated tumor cell sample (step (b) skipped).
1—Fresh human tumor samples (human gliomas of different grades) are received from the operating room, place in a recipient containing PBS1x.
2—The tumor sample is dissociated using Papain (3 mg/ml of activating solution Worthington) dissolved in activating solution (1.1 mM EDTA, 5.5 mM L-cysteine/HCl Sigma), and mechanistic chopping.
3—Incubation lasts 45 minutes.
4—Tumor pieces are then washed with media (DMEM-F12-Ham's Gibco) supplemented with Penicillin-streptomycin at 1/1,000 (Gibco).
5—The cell dissociation mixture is centrifuged at 1,200 rpm for 15 min at 4° C.

6—A mixture of 1:1 of ovomucoid inhibitor (0.7 mg/ml Worthington) and DNase 10 mg/ml is added to the cell pellet in order to inhibit proteases. The preparation is gently pipetted up and down until the mixture passes correctly into the tips. Media is finally added to a ratio ((1:1):8). If tumor pieces are not completely digested, the preparation is passed through a 70 μM cell scraper.

7—The preparation is then centrifuged at 1,200 rpm for 5 min at 4° C. The supernatant is discarded. The cell pellet is resuspended into 10 ml of media (DMEM-F12-Ham's Gibco) supplemented with Penicillin-streptomycin at 1/1, 000 (Gibco), centrifuged at 1200 rpm for 5 min at 4° C. This step is repeated twice.

8—½ of the cell pellet is taken up into 10 ml of media (DMEM-F 12-Ham's Gibco) supplemented with Penicillin-streptomycin at 1/1,000 (Gibco), serum free supplement B27 (1/50 Gibco) or serum free supplement BIT9500 (20% Stemcell Technologies), human recombinant EGF (20 ng/ml Invitrogen) and basic FGF-2 (20 ng/ml Invitrogen).

9—½ of the cell pellet is taken up into 4 ml of PBS1x for fresh analysis at the cell sorter FACSvantage SE.

10—The sorter is calibrated at 488 nm wavelength excitation, and cell autofluorescence emission is measured in the FL1 channel using either a 515 nm or 530 nm minors with a detector level up to 599 nm (but 450 nm is sufficient).

11—Addition of Trypan Blue (1/1,000 Sigma) in the PBS1x containing freshly dissociated tumor cells allows the identification of viable cells into the autofluorescent population (so called FL1$^+$) and the non-autofluorescent FL1 population (so called FL1$^0$. The measure is done in the FL3 channel with a 488 nm excitation laser, but can be done in the FL4 channel with either a 546 nm or a 632 nm excitation laser.

12—The protocol for analyzing cell is gated on viable cells, thus the cells display low FSC and low SSC, are excluded from the FSC-SCC R1 gating. This also includes red globuli.

13—The percentage of freshly dissociated FL1$^+$ cells is calculated into the entire population, which includes red globuli.

14—Because the FL1$^+$ and FL1$^0$ cell selections are specifically done on viable tumor cells (R1* FL1$^+$) and (R1* FL1$^0$), gates are specifically placed on FL1$^+$ and FL1$^0$ viable cells prior purification of the two sub-populations (FIG. 3).

Example 2

Figure 4:
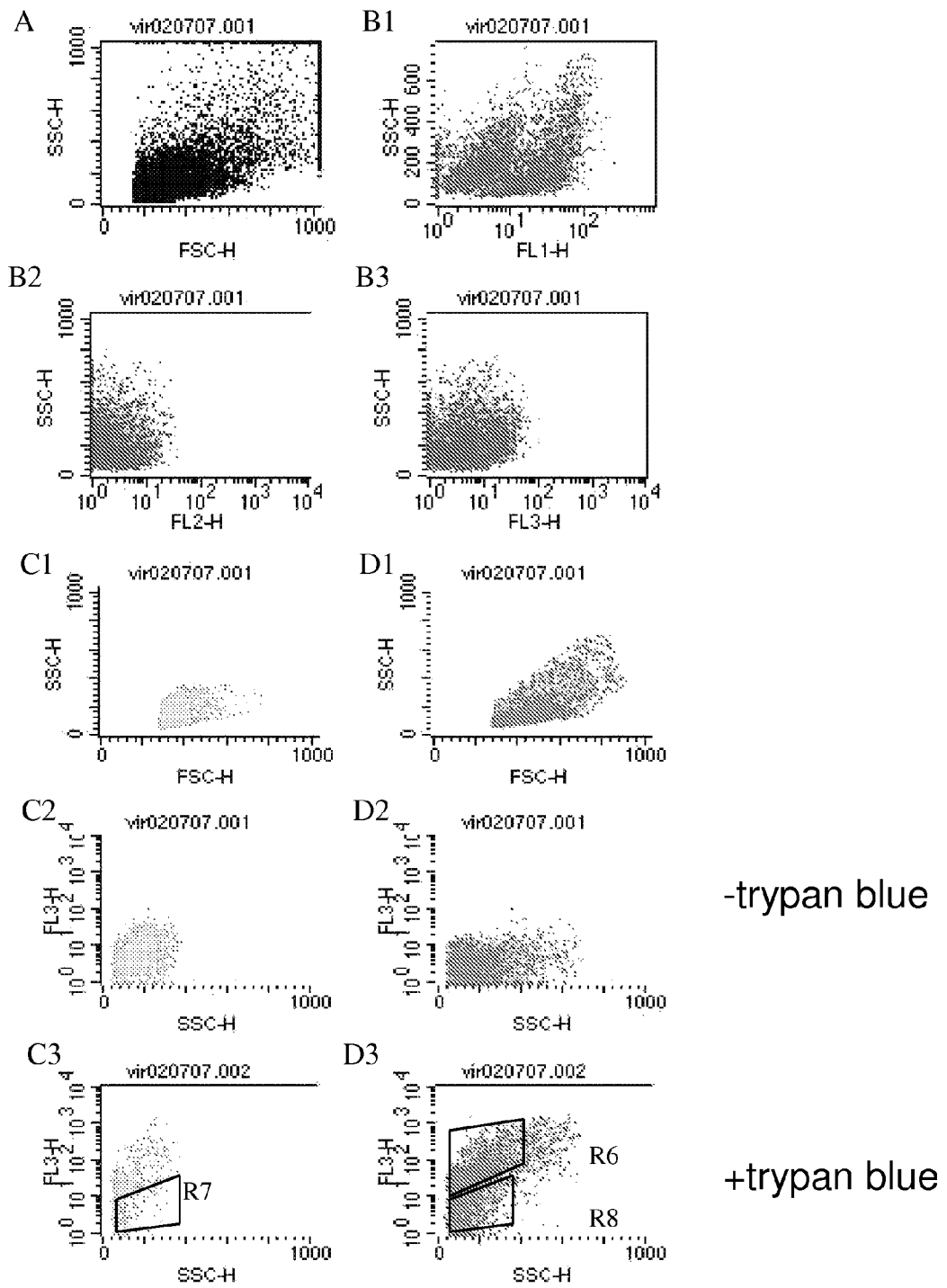
FIG. 4 shows a cell analysis performed on cells cultured in stem cell conditions as described in Example 2. (A) entire cell population. No gate. (B1-B3) R1 potential viable cells. (C1-C3) levels of autofluorescence in the FL1-H, FL2-H, FL3-H channels respectively. R2 viable $FL1^o$ C1: $FL1^o$ morphology, C2: $FL1^o$ fluorescence level without trypan blue, C3: $FL1^o$ fluorescence level after addition of trypan blue. (D1-D3) R3 viable $FL1^+$. D1: $FL1^+$ morphology, D2: $FL1^+$ fluorescence level without trypan blue, D3: $FL1^+$ fluorescence level after addition of trypan blue. R6: dead cells (in R1 gated population). R7: viable cells $FL1^o$ (in R1 gated population). R8: viable $FL1^+$ (in R1 gated population). The following results are observed: 93.3% of R1 gated cells are viable, among which ~21% are $FL1^+$ viable cells, ~23% are $FL1^o$ viable cells.

Method for Analyzing and Purifying Cancer-Initiating Cells Cultured in Stem Cell Conditions (FIG. 4)

The method according to the invention is performed on a tumor cell sample cultured in stem cell conditions (under step (b)).

1—Cells are obtained from the previously described protocol and cultures derived from the point 8-described above (8-½ of the cell pellet is taken up into 10 ml of media (DMEM-F12-Ham's Gibco) supplemented with Penicillin-streptomycin at 1/1,000 (Gibco), B27 (1/50 Gibco) or BIT9500 (20% Stemcell Technologies), human recombinant EGF (20 ng/ml Invitrogen) and basic FGF-2 (20 ng/ml Invitrogen)).

2—Culture is placed at 37° C. in a 5% $CO_2$ incubator for 48 hours.

3—The cell suspension is centrifuged at 1,200 rpm for 5 min at 4° C. The cell pellet is washed with PBS1x, centrifuged again, and the cell pellet is taken up into 1.1 ratio of conditioned media and stem cell media (DMEM-F12-Ham's Gibco) supplemented with Penicillin-streptomycin at 1/1, 000 (Gibco), B27 (1/50 Gibco) or BIT9500 (20% Stemcell Technologies), human recombinant EGF (10 ng/ml Invitrogen) and basic FGF-2 (10 ng/ml Invitrogen), 4—The conditioned media (CM) results from previous culture of cancer-initiating cell after centrifugation of cells when cells are passed (once a week). This CM is stored at −20° C., filtered through a 0.22 μm PES syringe filter prior being added to a new culture.

5—The same procedure of washing, centrifugation, and media replacement is repeated all along passages until spheres appears.

6—Once cells are starting to form spheres (so called gliomaspheres) as observed by microscopy, cells are mechanistically dissociated by mechanistic reflushing a maximum number of 5 times when renewing media, and passing cell at a dilution of 50,000 c/ml.

7—To analyse the percentage of FL1$^+$ and FL1$^0$ viable cells, cells are dissociated (see 6—), centrifuged 1,200 rpm for 5 min at 4° C., washed in PBS1x, and taken up into 4 ml of PBS1x.

8—The sorter is calibrated at 488 nm wavelength excitation and cell autofluorescence emission is measured in the FL1 channel at 515 or 530 nm with a detector level up to 599 nm.

9—The protocol for analyzing cell is gated on viable cells. Addition of Trypan Blue (1/1,000 Sigma) in the PBS1x containing dissociated tumor cells allows the identification of viable cells into the autofluorescent population (so called "FL1$^+$") and the non- autofluorescent FL1 population (so called "FL1$^0$ "). The measure is done in the FL3 channel with a 488 nm excitation laser, but can be done in the FL4 channel with either a 546 nm or a 632 nm excitation laser.

10—The percentage of dissociated FL1$^+$ cells is calculated into the entire viable population (R1).

11—Because the FL1$^+$ and FL1$^0$ cell selection is specifically done on viable tumor cells (R1* FL1$^+$) and (R1* FL1$^0$), gates are specifically placed on FL1$^+$ and FL1$^0$ viable cells prior purification of the two sub-population (FIG. 4)

Example 3

Figure 6:
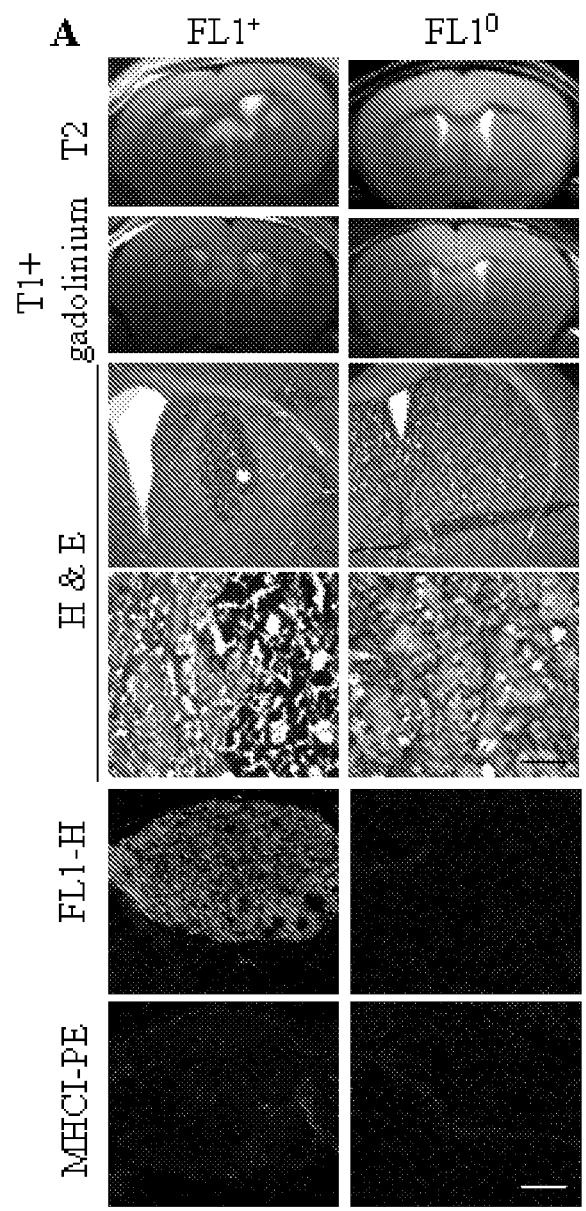
FIG. 6 shows that $FL1^+$ cells initiate and sustain tumor growth in vivo. (A) In vivo imaging and histological analyses of mice implanted with $FL1^+$ or $FL1^o$ sorted cells ($10^5$ cells were implanted), such as described in Example 3. Representative sequence images of brain implanted mice upon Magnetic Resonance Imaging (RMI) prior—(T2), and post-contrast (T1+gadolinium). Hematoxylin and Eosin (H&E) staining of implanted brain slices (2.5×), and at higher magnification (20×). FL1-H autofluorescent (light gray) and co-localisation with MHCI allows the identification of the tumor cells from human origin (10×). (B) Expression analyses of GFAP-, NESTIN-, TUJ1-, Ki67- expressing cells in the FL1 implanted mice. DAPI stained nucleus (blue). Scale bar: µm. (C) Pictures of gliomaspheres derived from $FL1^+$ and $FL1^o$ injected mice. Injected and contralateral side of mouse brain bearing tumors were dissociated and analysed by FACS for autofluorescence FL1- H levels prior to in vitro culture. Cell culture derived from the contralateral side of $FL1^+$ injected mice revealed the formation of gliomaspheres, $FL1^+$, indicating the migration capacity of $FL1^+$. Scale bar: µm. (D) Table summary for the number of nude mice implanted with $FL1^+$ and $FL1^o$ -sorted cells from various gliomasphere cultures (N=24 and N=23 respectively). (E) Table shows the number of nude mice implanted with prospectively isolated $FL1^+$ and $FL1^o$ -sorted cells ($40^3$ cells/mouse).
Figure 6:
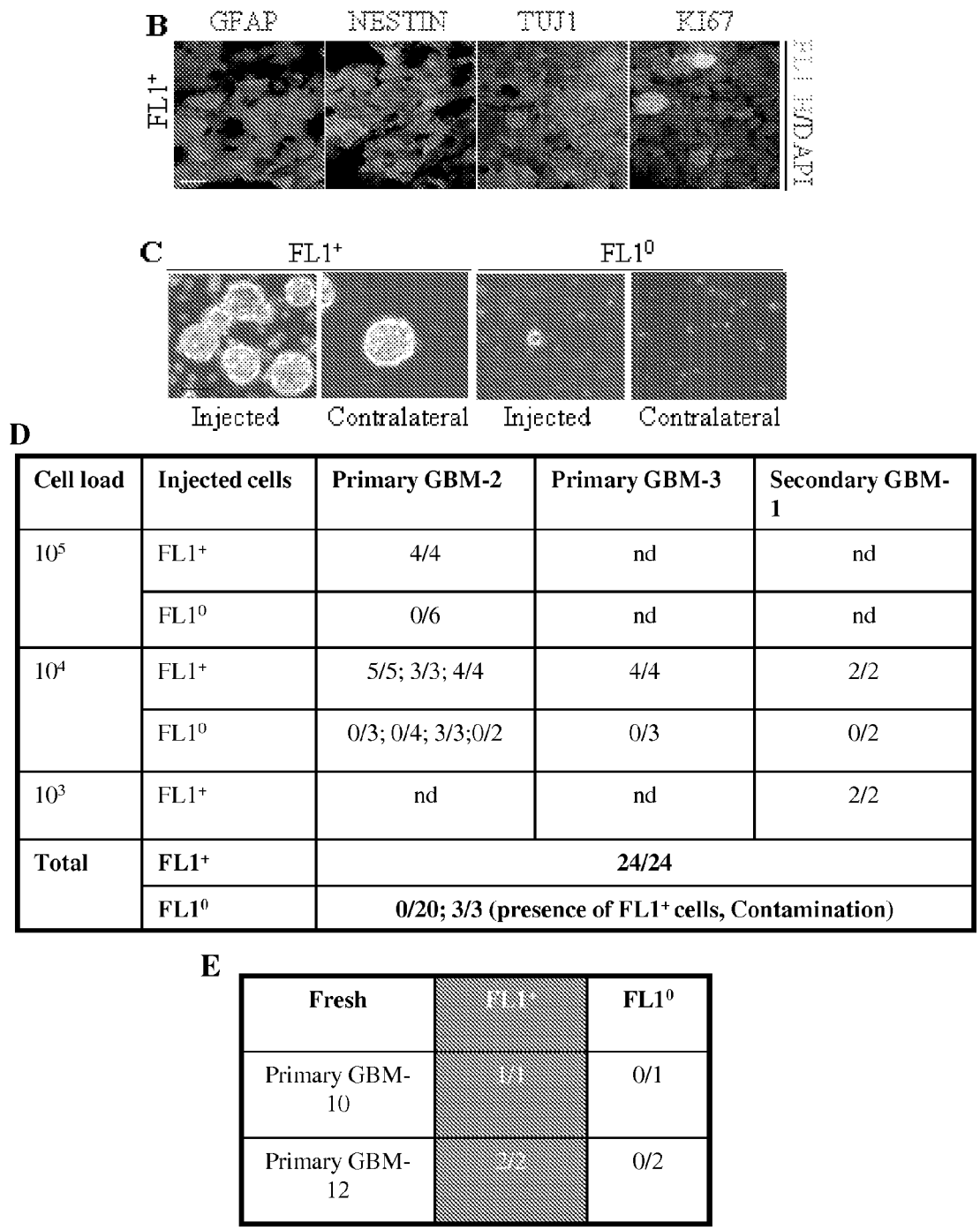

Further Characterization of the Properties of the Identified and Purified Immature and Stem-Cell Initiating Cell Sub-Populations Obtained by the Method According to the Invention (FIG. 6)

The isolated cell sub-populations (FL1$^0$ and FL1$^+$) obtained by the method according to the invention are characterized in vitro according to standard protocols. Examples of in vitro characterization (such as stemness properties such as spherogenic potential and multipotency) are provided below and on FIGS. 2, 5 and 12. Further, the in vivo properties (such as tumorigenic potential) of those cell sub-populations are tested according to standard protocols. Examples of in vivo properties are provided below and on FIG. 6. In the present study, a subpopulation of human glioma cells that display a distinct morphology and a specific autofluorescence emission in the FL1 channel upon 488 nm laser excitation has been isolated. This cell fraction, called FL1$^+$, is detected both by fluorescent microscopy (FIG. 11) or fluorescent activated cell sorting FACS (FIG. 3,4). FL1$^+$ cells are detected as a small subpopulation in human freshly dissociated cells from glioma tissues (0.15-21%, N=11) irrespectively of tumor grade and type. After culture in stem cell enriching conditions, glioma cells form floating colonies called gliomaspheres, that show higher fractions of $FL1^+$ cells (4-60%, N=7). When comparing cultures from different tumor grades, the $FL1^+$ fraction remains variably stable over 10 passages (FIG. 10, FIG. 9B).

Figure 7:
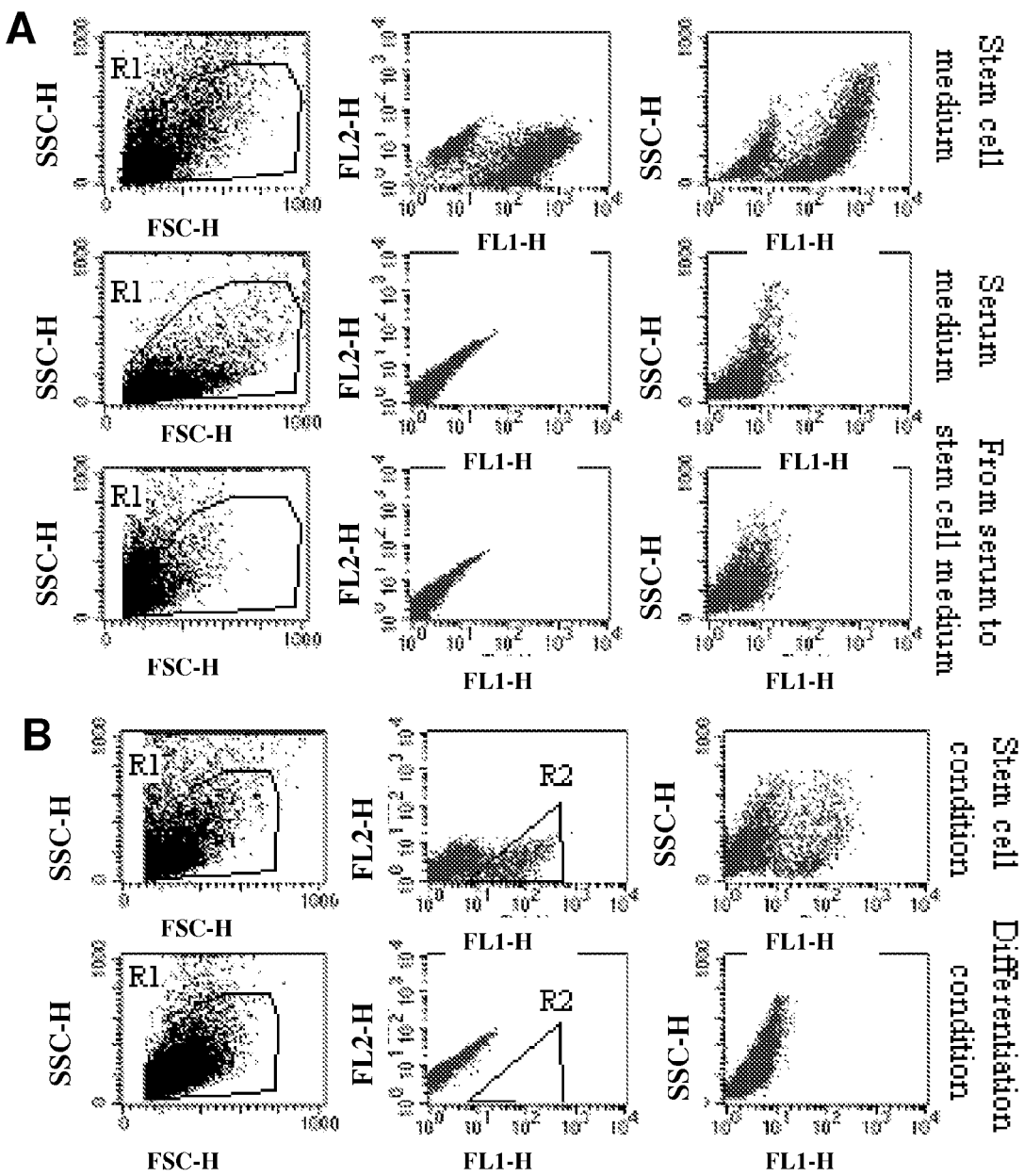
FIG. 7 shows that fresh glioma tumor and glioma stem cell cultures contain an FL1-H auto-fluorescent population. (A) FACS analysis of primary GBM IV-2 cells cultured in different media conditions since tumor dissociation. Top panel: primary GBM IV-2 cells cultured in stem cell conditions, harboring the presence of an $FL1^+$ cell population. In contrast, when the same primary GBM IV-2 cells were initially cultured in serum-rich conditions (middle panel), no $FL1^+$ autofluorescent cells were observed instead, a homogeneous cell population with a low autofluorescence was monitored by FACS. The primary GBM IV-2 cells were transferred and cultured from serum-rich media to stem cell media for 4 passages. However, cells do not recover any FL1-H autofluorescence. A single cell population with low FL1-H autofluorescence levels remains, suggesting that primary GBM IV-2 cells have irreversibly lost their $FL1^+$ population in serum. (B) FACS analysis of primary GBM IV-2 cells cultured first, in stem cell conditions (top panel) and then, plated for differentiation on Poly- Ornithine-Laminin substrate without mitogens for 7 days (bottom panel). R2 gates the percentage of FL1-H positive cells. Withdrawal of mitogens only or plating in serum-rich conditions (data not shown) is not sufficient to abolish the $FL1^+$ autofluorescent cell population unlike the differentiation assay. Tumor sample type legends are on FIG. 9A.
Figure 8:
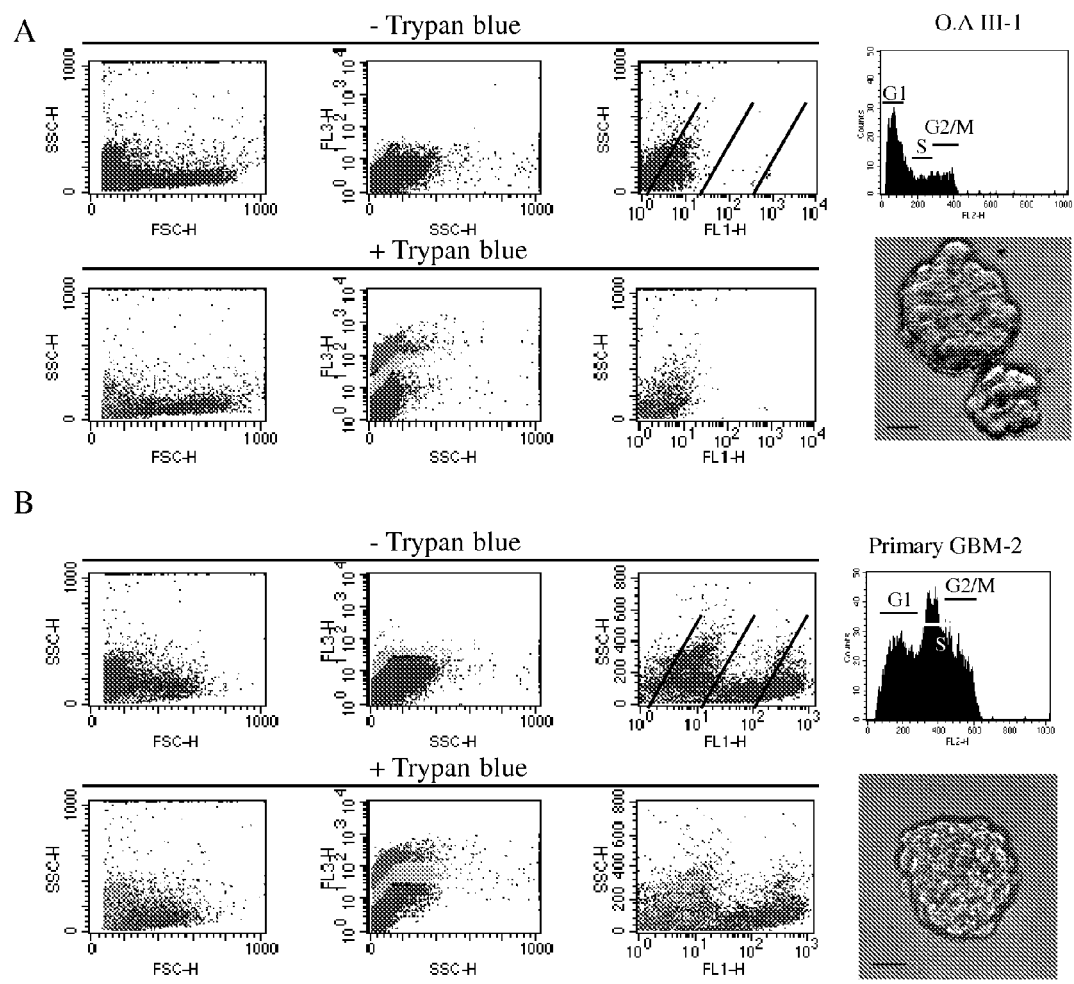
FIG. 8 shows the morphology and fluorescence levels in FL1, and FL3 after addition of trypan blue, the cell cycle and pictures of two gliomasphere cultures. (A) A.O.III-1 and (B) primary GBM-2.
Figure 12:
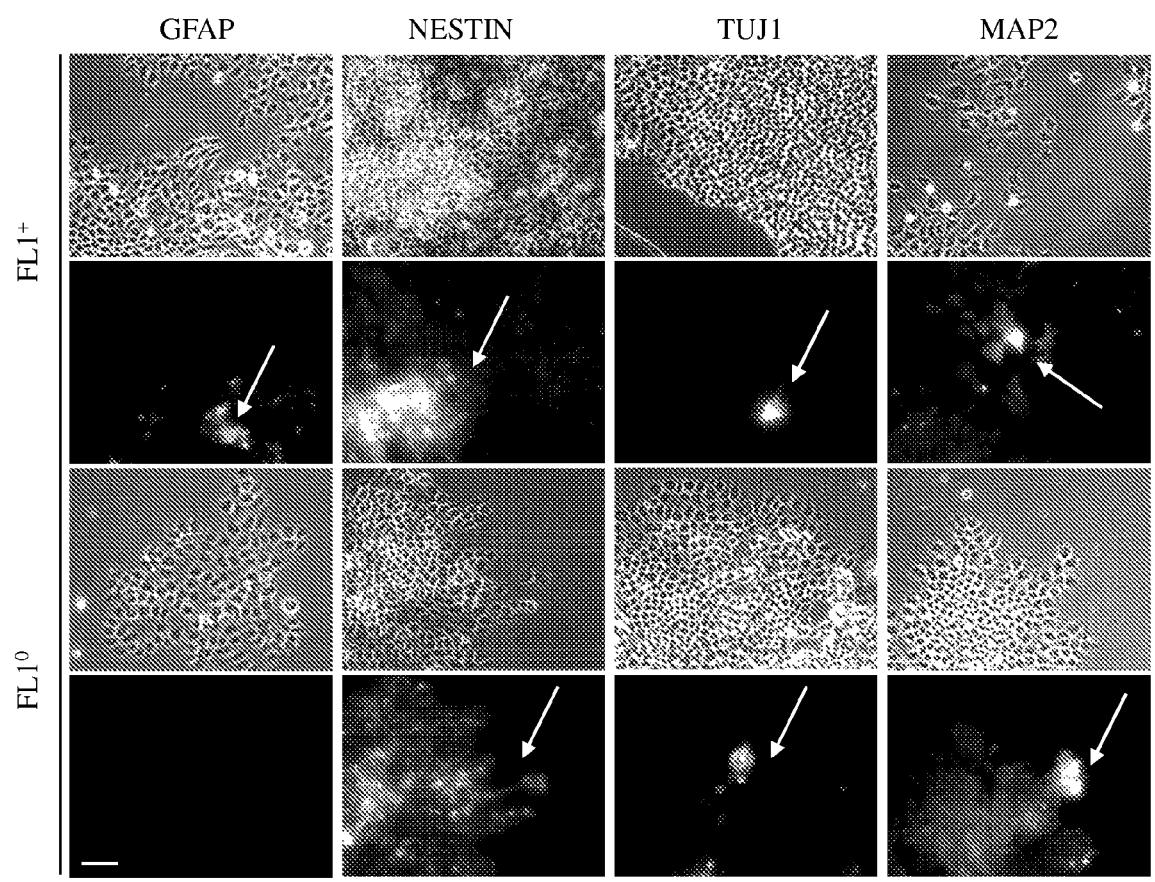
FIG. 12 shows that FL1$^+$ and FL1$^0$ cells can differentiate into different neural lineages Purified FL1$^+$- and FL1$^0$-cells from primary GBM-2 gliomasphere were plated for differentiation during 10 days. Cells were fixed, and stained for GFAP, NESTIN, TUJ1, and MAP2. Note that FL1$^+$ and FL1$^0$ cells do differentiate to similar extend, indicating their multipotency capability. Few cell islets were positive for GFAP (2-3% of cells). 1% of TUJ1 positive cells were detected upon induction of differentiation. Although basal levels and percentages of MAP2- or NESTIN-expressing cells were higher compared to the one of GFAP- and TUJ1-expressing cells, only 10-15% of cells were highly positive for MAP2 or NESTIN. Arrow points the positive cells. Scale bar: 80 μm.

However, when freshly isolated glioma cells are plated in serum-containing, non-stem cell conditions, no $FL1^+$ fraction could be detected, nor could subsequent transfer to stem cell culture conditions recover a $FL1^+$ population or initiate sphere formation (FIG. 7A). In contrast, priming of glioma cells as gliomaspheres in stem cell medium prior to culture in serum media was sufficient to maintain a $FL1^+$ fraction that can initiate secondary sphere even in serum media (data not shown). Furthermore, gliomaspheres primarily cultured in stem cell conditions irreversibly lose their $FL1^+$ fraction as well as their clonogenic ability upon induction of differentiation (FIG. 7B, FIG. 12). These experiments suggest that $FL1^+$ cells might be associated with stemness properties in gliomaspheres.

As self-renewal is a landmark of stemness in normal tissues and cancer, the ability of $FL1^+$ and non FL1 cells)($FL1^0$ to self-renew by forming new spheres in clonal assays has been tested for various tumour samples (FIG. 9A). After purification by FACS, $FL1^+$ and $FL1^0$ cells were plated as single cells in stem cell conditions and counting of secondary spheres showed a significantly higher spherogenic potential in $FL1^+$ cells (FIG. 2A). To compare the long term self-renewal ability, the spherogenicity of individual $FL1^+$ and $FL1^0$ clones was measured along successive passages. While $FL1^+$ clones retained significant and stable spherogenic potential over up to five passages, $FL1^0$ clones were lost between passage 3 and 4 and no clone was anymore able to sustain new sphere formation at passage 5 (FIG. 2B). The morphology of $FL1^+$ and $FL1^0$ spheres was significantly different, $FL1^+$ spheres being bigger, floating and appearing healthier than partially attached and undersized $FL1^0$ clones (FIG. 2C). These clonal assays convincingly demonstrate that the long term aptitude to self-renew is selectively restricted to a $FL1^+$ compartment in human glioma. Nevertheless, $FL1^0$ cells are also initially viable tumor cells as they are found not only in freshly dissociated glioma tissue but also in clonal gliomaspheres where they cohabitate with $FL1^+$ cells and can be sorted and passaged (as spheres) several times. Because non-sorted but clonal gliomaspheres contain a mixed population of $FL1^+$ and $FL1^0$ cells and because $FL1^+$ cells have a higher spherogenic potential, $FL1^0$ cells should logically be daughter cells derived from $FL1^+$ cells by asymmetric division or by loss of $FL1^+$ properties. Analysis of $FL1^+$ fractions in unsorted gliomaspheres and in sorted $FL1^{+\ and\ FL}1^0$ clones derived thereof shows after 4 passages that $FL1^+$ derived spheres contain again a mixed $FL1^+$ and $FL1^0$ population. In contrast, $FL1^0$ derived cultures do not recover significant $FL1^+$ cells. This provides evidence that $FL1^0$ cells derive from the $FL1^+$ population, remain viable for several passages but could not in turn reacquire autofluorescent properties once they have switched from the $FL1^+$ toward the $FL1^0$ state (data not shown). Therefore, it is suspected that $FL1^0$ cells are committed progenitors or differentiating cells, which have lost their self-renewal and tumorigenic properties.

Figure 11:
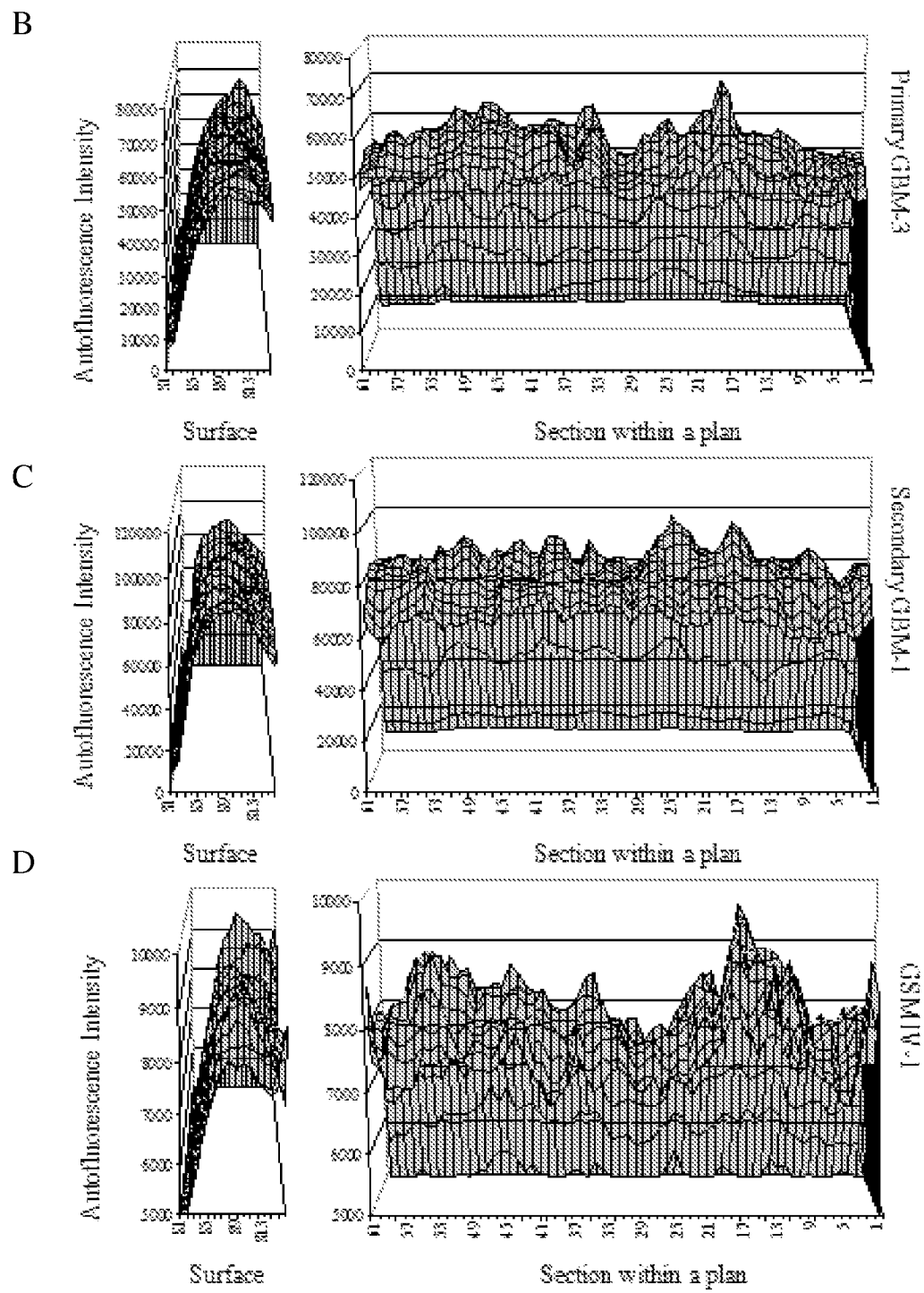
FIG. 11 shows the quantification of protein markers within gliomaspheres after confocal 3D reconstruction. (A) The diagram shows the procedure to quantify and tabulate the expression and localization of individual marker with the FL1 autofluorescence within a gliomasphere. Specifically, the left scheme indicates the Z-stack sections after confocal microscopy, which allows the tabulation of the expression and localization of protein per surface (X axis of the left graph panel B to K). The right scheme represents the quantification of protein expression and localization within a 6°-sector for a given surface. The analysis of 60 sectors per surface corresponds to the X axis of the right graph (section within a plane) panel B to K. (B-D) Quantification of FL1 autofluorescence levels in 3 different gliomasphere cultures. Note the greater intensity of FL1 autofluorescence inside the sphere (left graph), and the heterogeneous expression and localization per sector amongst the different surfaces (right graph). (E-M) Quantification of the expression level and localisation of individual markers within primary GBM-3 gliomaspheres (left and middle graphs). Percentage of marker-expressing cells within unsorted primary GBM-3 cells (top right), FL1$^+$-sorted cells (middle right), FL1$^0$-sorted cells (bottom right). Markers studied were: NANOG (E), OCT4 (F), SOX2 (G), KI67 (H), NOTCH1 (I), NESTIN (J), GFAP (K), PDGFRα (L), Integrinβ1 (M).
Figure 11:
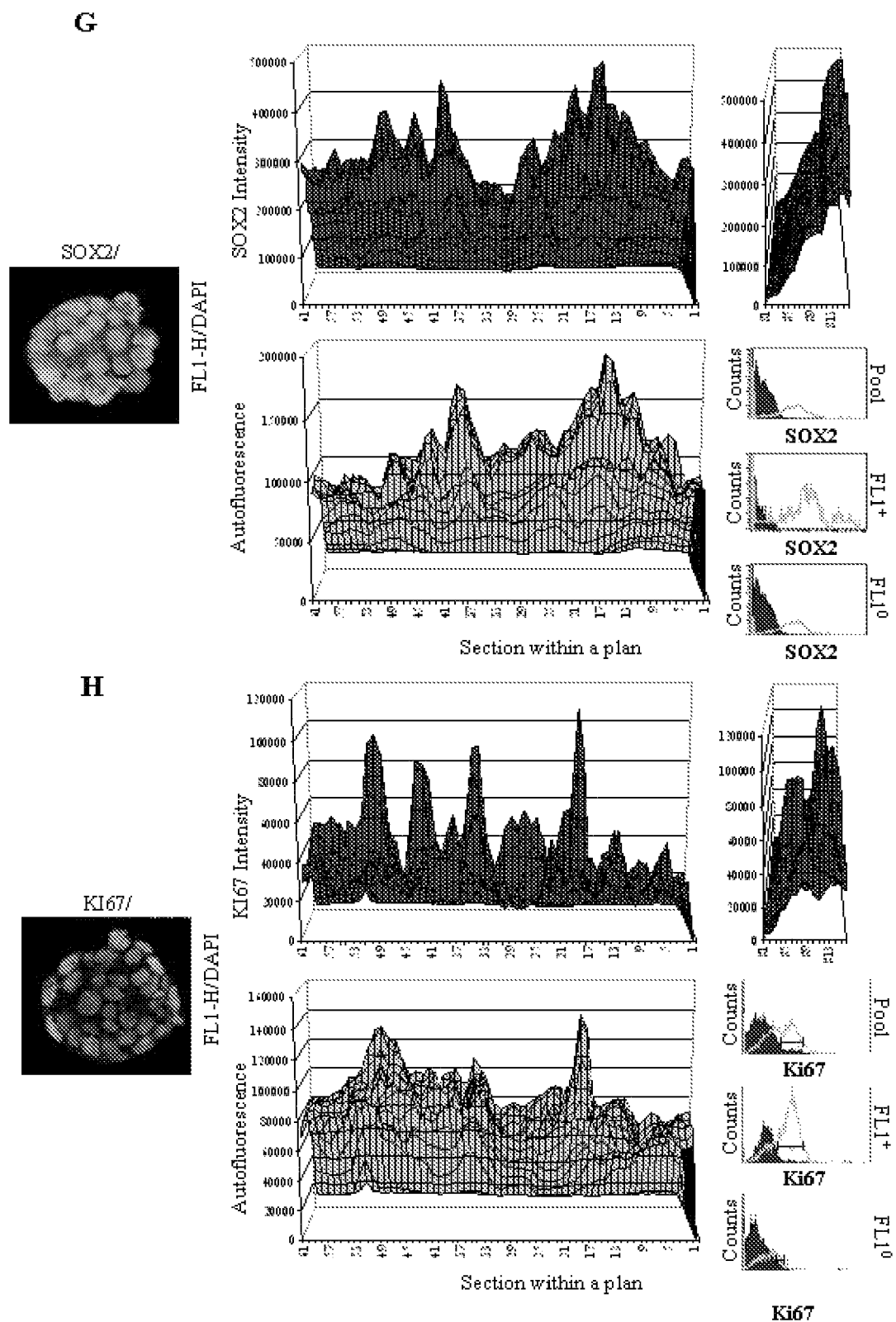
Figure 11:
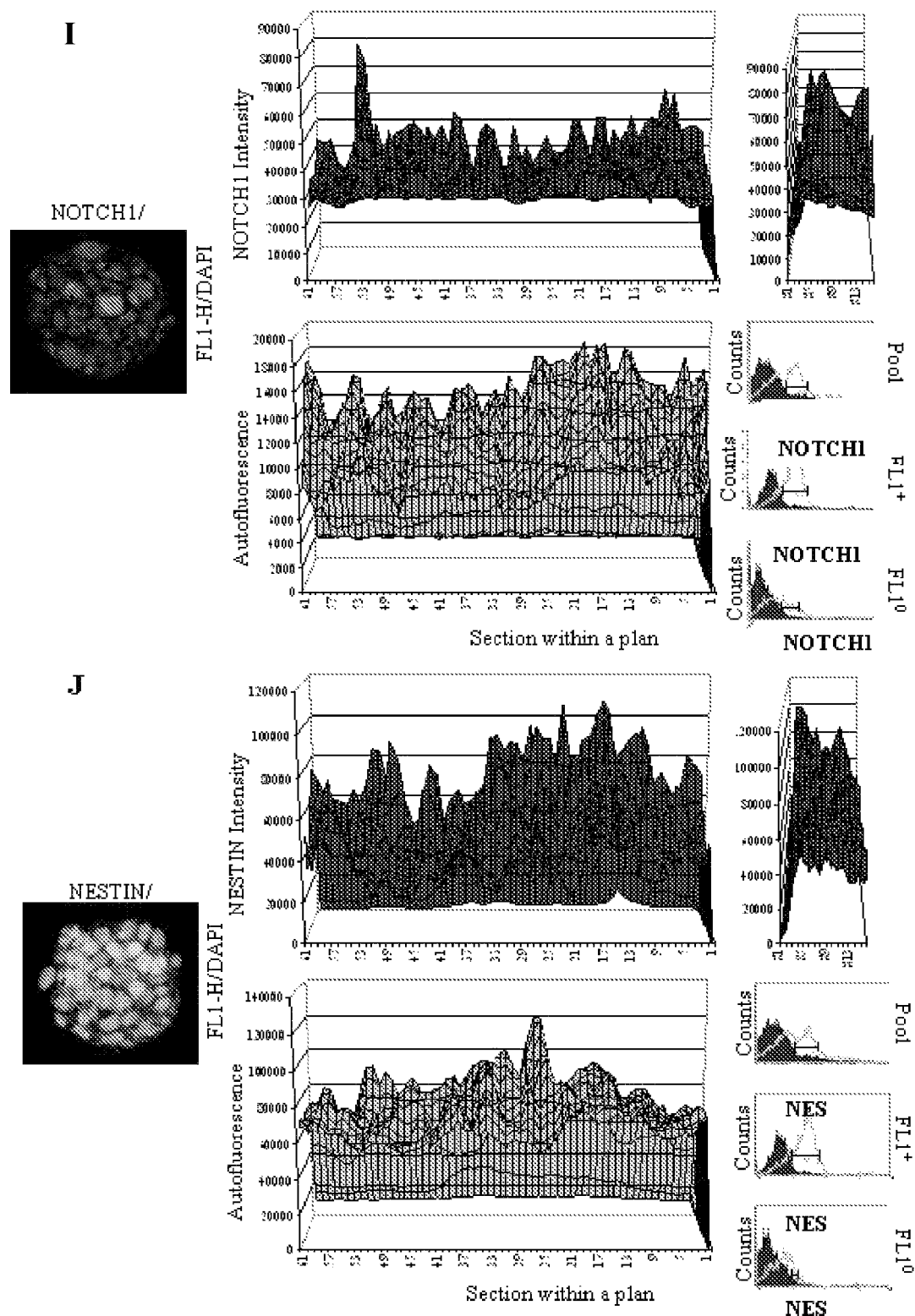
Figure 11:
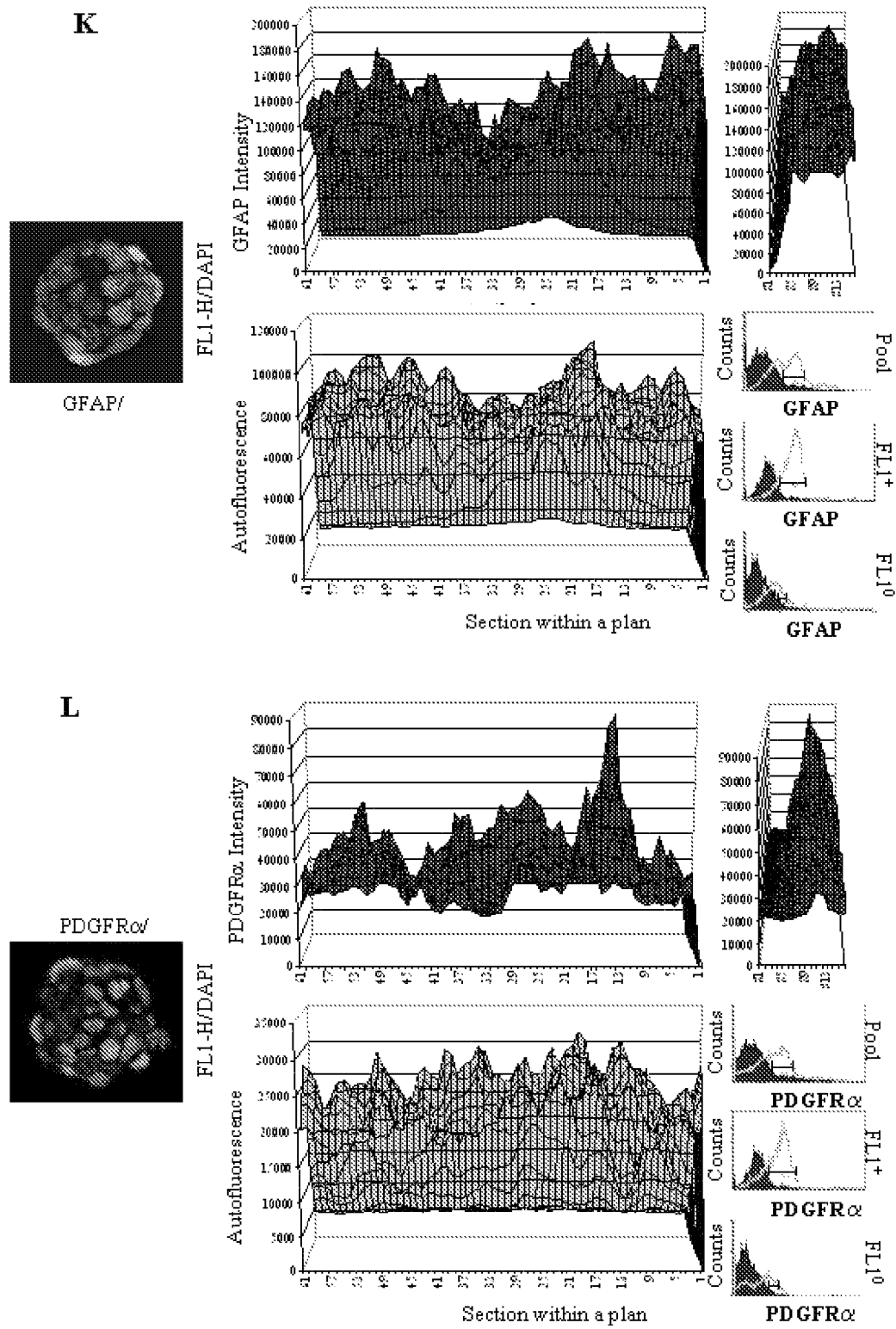
Figure 11:
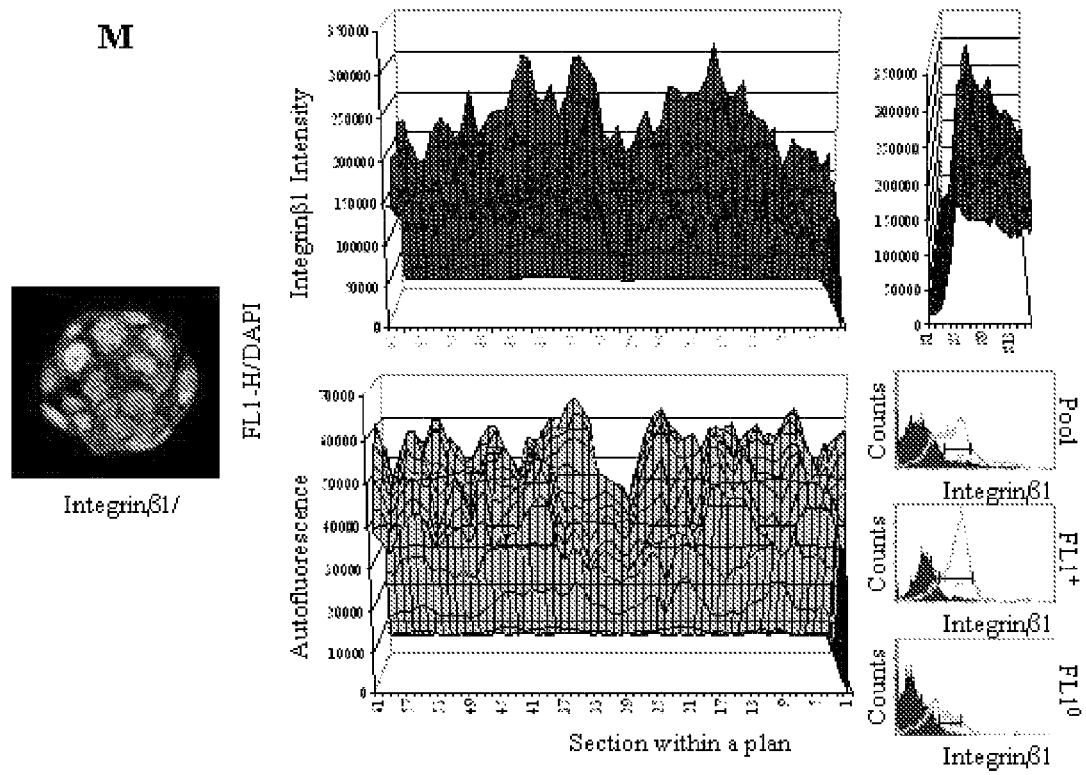

Several stem cell or progenitor signature profiles have been identified in glioma or their putative cancer stem cells (Clement et al., 2007, *Curr. Biol*, 17, pages 165). Moreover, several developmental pathways have been shown to play an important role in glioma and their stem cells such as the sonic hedgehog-gli (Clement et al., 2007, above), Notch 1 (Fan et al., 2006, *Cancer Res.*, 66, 7445). In order to understand the molecular mechanisms underlying the selective sterness phenotypes of $FL1^+$ glioma cells, the expression of a selection of 11 stemness related genes in $FL1^+$ and $FL1^0$ cells from 4 different gliomas has been tested. While NANOG, OCT-4, SOX-2, NOTCH-I, and NESTIN are significantly overexpressed (>2x) in $FL1^+$ cells of at least 3 out of 4 different gliomas tested, the expression of PDGFR-αPTEN, INTβ-1, OLIG-2, ABCG-2, BMI-I did not change significantly (FIG. 5A). These changes do not seem related to a difference in cell proliferation since PCNA did not show significant variation between $FL1^+$ and $FL1^0$ cells. The expression of the stemness genes, and their co-regionalisation with $FL1^+$ autofluorescent cells were then tested using immunohistochemistry and confocal imaging in gliomaspheres. Although the distribution of individual stemness genes was only partially overlapping with $FL1^+$ cells, NANOG, OCT-4, SOX-2, NOTCH-I, and NESTIN showed preferential co-regionalisation and -localization with $FL1^+$ cells. (FIG. 11). The fact that most of the enriched stemness genes in $FL1^+$ populations are also detected in $FL1^0$ cells and that some $FL1^+$ cells in gliomaspheres do not express individual stemness proteins otherwise expressed in a majority of $FL1^+$ is relevant for the use of any of these stemness genes as putative molecular stem cell markers. In addition, Ki67 was used as a marker of index proliferation, showing that all $FL1^+$ cells are $Ki67^+$ yet all $Ki67^+$ are not $FL1^+$ (FIG. 11). Because Ki67 antigen is the prototypic cell cycle related nuclear protein, expressed by proliferating cells in all phases of the active cell cycle (G1, S, G2 and M phase), these results indicate that $FL1^0$ cells are viable and do proliferate. However, a more accurate analysis of cell cycle revealed that the majority of $FL1^+$ cells are in S-G2/M phase while the majority of $FL1^0$ cells are in G1 metabolic phase (FIG. 5B). Because several studies have linked autofluorescence with cellular metabolic activity such as NAD/NADPH+ status, or mitochondrial flavin content, mesenchymal stem cells (Schuchmann et al., 2001., *Brain Res. Brain Res. Protoc*, 7, pages 267; Reyes et al, 2006, *Stem Cells*, 24, pages 1213; Kann et al., 2003, *Neuroscience*, 119, pages 87), the metabolic activity of $FL1^+$ and $FL1^0$ cells using an oxido-reduction colorimetric assay (CellTiter 96® $AQ_{ueous}$ One Solution Cell Proliferation Assay from Promega containing MTS and an electron coupling reagent (PES)), based on the activity and ratio NAD/NADPH+ enzymes has therefore been tested. A significantly higher metabolic activity (dark grey) was found $FL1^+$ -sorted cells compared $FL1^0$ -sorted cells in 4 out of 4 tested gliomas (FIG. 5C). A clear correlation is consequently observed between metabolic activity, percentage of cells S/G2-M phase, and levels of autofluorescence, yet it remains unclear how autofluorescence reflects stemness potential of a subpopulation of glioma cells.

If only $FL1^+$ glioma cells display stemness properties such as self-renewal and multipotency in vitro, glioma-initiating cells should plausibly be found within the $FL1^+$ population. To test this possibility, nude mice (N=47) were implanted intracranially with a load of $10^3$, $10^4$ and $10^5$ $FL1^+$ or $FL1^0$ cells sorted from various gliomasphere culture (FIG. 6). At 4 weeks post-implantation, 100% of $10^5$ $FL1^+$ cells injected mice have developed significant weight loss and neurological symptoms that were correlated with intracranial tumors on MRI and histological sections, all of which were significantly bigger than the one observed in a mouse implanted with $10^5$ unsorted cells from gliomaspheres (FIG. 6). Although the symptom-free survival was longer, all of $10^4$ $FL1^+$ implanted mice also developed symptoms by 6 weeks post- implantation. In contrast, no tumor was ever seen in any of the $FL1^0$ injected mice, even at a $10^5$ intracranial cell load after more than 3 months observation. Remarkably, all tumors showed a bright autofluorescence when observed with a confocal microscope as opposed to normal non-tumoral adjacent mouse tissue. Immunohistochemical analysis showed that $FL1^+$ induced tumors express GFAP, NESTIN, and some TUJ1 and have a high proliferative index visualized by Ki67staining The human origin of tumor cells was confirmed by specific MHCI staining (FIG. 6A), and allowed the double selection of MHCI+, FL1-H cells. Plating of in vivo-dissociated cells in stem cell conditions reveal the formation of numerous and large spheres derived from $FL1^+$ implanted brains as opposed to cultures from $FL1^0$ implanted brains, confirming and extending the incapacity of $FL1^0$ to revert into $FL1^+$ cells in vivo, and confirming that $FL1^+$ can be passaged in vivo (FIG. 6C). Therefore, these data clearly demonstrate the exclusive in vivo tumorigenic potential of $FL1^+$ cells.

The expression of the unique stem cell marker, CD133, was tested and it showed that CD133-expressing cells are distributed within both $FL1^+$ and $FL1^0$ cell compartments. CD133 marker may be useful for enriching self-renewing cells in the $FL1^{+/0}$ fractions, its significant benefit was found in 2/2 fresh gliomas and in 2/5 GIC cultures (efficiency: 57%). Therefore, CD133 cells do represent only a sub-population of the tumor-initiating cell reservoir, and confirms that the unique and exclusive use of CD133 as a stem cell marker is inappropriate and not essential. As opposed, the FL1 phenotypical criteria according to the invention turns out to be a very reliable method for isolating self-renewing cells in 8/8 fresh gliomas and 7/7 GIC cultures (efficiency: 100%).

In summary, properties of $FL1^+$ and $FL1^0$ cells are summarized under FIG. 13 and molecular investigations and characterizations revealed that $FL1^+$ cells:
- are tumorigenic
- can generate $FL1^0$ cells and are responsible for maintaining the GICs culture overtime
- are multipotent
- are enriched for stemness-related genes at the RNA level but the distribution of the stemness-related proteins is equally distributed within $FL1^+$ and $FL1^0$ daughter cells
- contain more than >40% of actively dividing cells (in G2/M phase)
- harbor a huge metabolic activity (NADH, LDH contents, typically at least two fold NADH levels for $FL1^+$ compared to $FL1^0$ and at least three fold LDH levels for $FL1^+$ compared to $FL1^0$).

Taken together, these in vitro and in vivo findings suggest that self renewing and tumor initiating glioma cells have a distinct autofluorescent phenotype that can be efficiently exploited to identify and isolate them. Moreover, these data suggest that this phenotype reflects a higher metabolic state and is associated with preferential expression of a stemness gene and protein profile in glioma initiating cells.

The method according to the invention based on specific autofluorescence allows fast, accurate and robust selection of glioma initiating cells that can considerably facilitate their characterization comparing to the use of one single molecular marker.

It has been suggested that a stem cell or early progenitor population is rarely defined only by one but rather by a combination of molecular markers. One single marker would therefore likely fail to specifically confine a stem cell compartment in gliomas. Interestingly, none of the stemness genes that could potentially be used as functional markers of cancer stem cells was exclusively confined to the $FL1^+$ population and could therefore hardly be used as a single stem cell marker (FIG. 6).

It might therefore be more appropriate to consider stemness potential in a given sub-population or single cells as a probability rather than an on/off state.

Example 4

Figure 14:
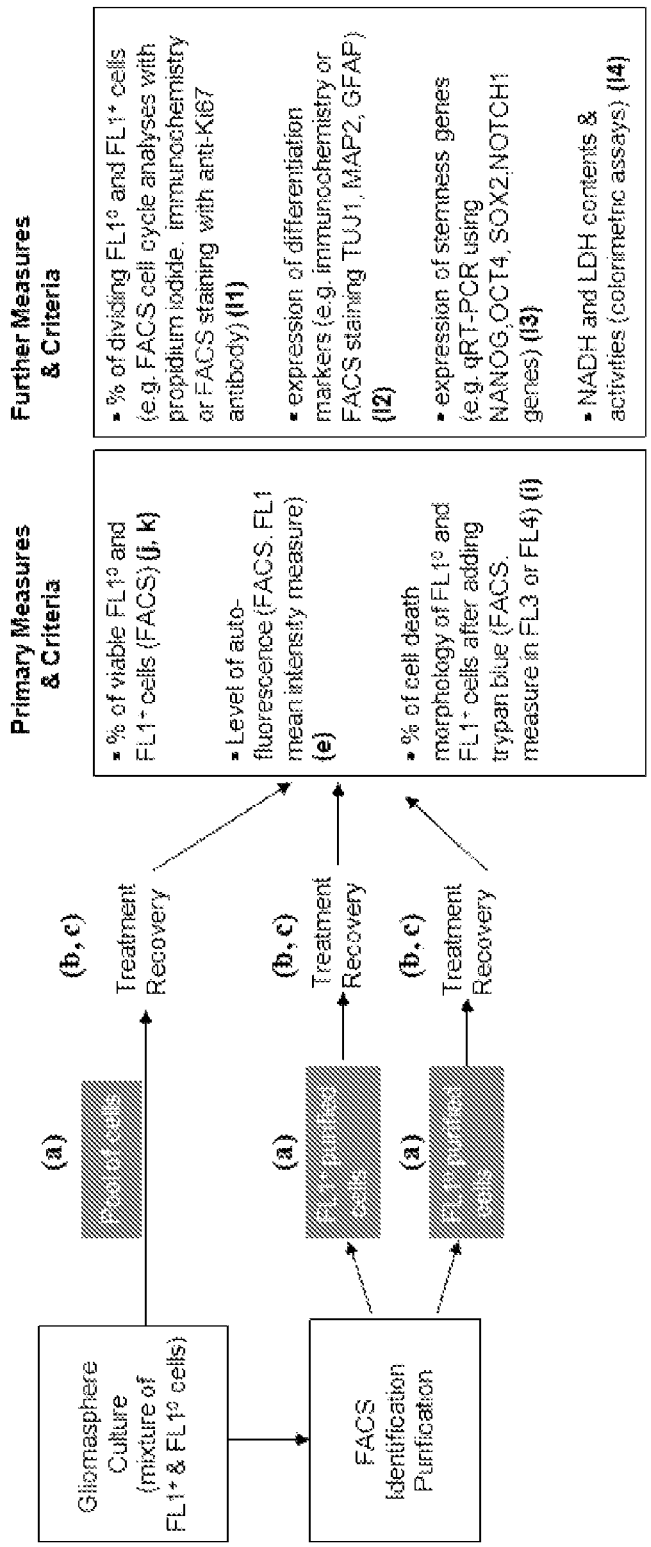
FIG. 14 represents a scheme for a method for detecting the recurrence of cancer stem cells in a cancer stem cell sample according to the invention. Steps (a), (b), (c), (i), (j), (k), (l1)-(l4) of the method of the invention are indicated.

In Vitro Recurrence Screening Assay on Cancer Cells Cell Sub-Populations Obtained by the Method According to the Invention (FIGS. 13 and 14)

A method according to the invention is carried out in order to detect in vitro recurrence of cancer stem cells such as described on FIG. 14.

Cancer stem cells as prepared according to the method of the invention ($FL1^+$, unsorted $FL1^+$ and $FL1^0$, $FL1^0$ cells) are provided (step (a)) are subjected to an anticancer treatment every 2.5 days (10 cell/µl) in presence of reduced growth factor (EGF and bFGF) concentration (e.g. 1 ng/ml) (step (b)). This anticancer treatment is for example selected from commonly used anticancer treatments such as radiotherapy (e.g. gamma irradiation) and chemotherapy (e.g. anti-cancer drug candidate addition). Treated cells are incubated in a stem cell culture medium for an incubation period without treatment (step (c)) Recovery starts when the treatment is stopped and once cells are transferred back into stem cell culture medium. During the incubation period (e.g. at day 5, 10 and day 20 after the last day of treatment), the following parameters are measured:
- percentage of cell death measured as described in Examples 1-3 (step (h));
- mean level of autofluorescence measured as described in Examples 1-3 (step (i));
- percentage of viable $FL1^0$ and $FL1^+$ cells selected on fluorescence and morphological criteria as described in Examples 1-3 (steps (f), (g), (j) and (k));
- detecting the spherogenicity of $FL1^0$ and $FL1^+$ cells as measured as described in Examples 1-3 (step l);
- expression of differentiation markers (ex: TUJ1, MAP2, GFAP) measured as described in Examples 1-3 (step 11);
- expression of stemness genes (ex: NANOG, OCT4, SOX2, NOTCH1) measured as described in Examples 1-3 (step 12);
- percentage of dividing $FL1^0$ and FL1+ cells (ex: cell cycle analyses with propidium iodide, staining with anti-Ki67 antibody) measured as described in Example 3 (step 13).
- determining the metabolic activity of $FL1^+$ and $FL1^0$ cells through the measurement of NADH and LDH contents and activities measured as described in Examples 1-3 (step 14).

The recurrence level is assessed on the basis of the measured parameters. Therefore, ability of anticancer treatments in removing $FL1^+$ cells from the cancer stem cell sample is inversely proportional to the measured recurrence level.

The invention claimed is:
1. A method for the preparation of a cell composition, comprising the steps of:
    (a) Providing a tumor cell sample;
    (b) Optionally culturing the cells provided in (a) in a culture medium;
    (c) Isolating in a sub-sample the cells which present autofluorescence emission detected at or about 520 nm upon laser beam excitation at a wavelength of or about 488 nm by fluorescence activated cell sorting, from the cells provided under step (a) or (b);
    (d) Isolating in another sub-sample by fluorescence activated cell sorting, the cells which are not fluorescent under step (c) and which present a positive shift in the fluorescence detected at >630 nm;

(e) Excluding dead cells from each of the isolated cell sub-sample obtained under steps (c) and (d);

(f) Pooling the cell sub-sample obtained under step (c) after treatment under step (e);

(g) Pooling the cell sub-sample obtained under step (d) after treatment under step (e).

2. The method according to claim 1 wherein the cells isolated under step (c) are those which further present a high Forward Scatter and a low/middle Side Scatter morphology under fluorescence activated cell sorting.

3. The method according to claim 1 wherein the cells isolated under step (d) are those which further present a low/middle Forward Scatter and middle/high Side Scatter morphology under fluorescence activated cell sorting.

4. The method according to claim 1, wherein the autofluorescence emission detected under step (c) is detected at or about 520 nm with a dichroïc mirror at 530 nm +/−15 nm.

5. The method according to claim 1, wherein the autofluorescence emission detected under step (c) is detected at or about 520 nm with a dichroïc mirror at 515 nm +/−5 nm.

6. The method according to claim 1, wherein dead cells are excluded under step (e) by trypan blue addition to the sub-samples obtained under steps (c) and (d).

7. The method according to claim 1, wherein the tumor cell sample provided under step (a) is a sample wherein the cells have been cultured after dissociation from a tumor sample.

8. The method according to claim 1, wherein the tumor cell sample provided under step (a) is dissociated from a tumor sample wherein the tumor sample is a tumor tissue obtained from a biopsy.

9. The method according to claim 1, wherein the culture medium under step (b) is selected from the group consisting of a stem cell medium, a serum rich medium and a differentiation culture medium.

10. The method according to claim 1 wherein the tumor cell sample provided under step (a) is a sample where cells have been dissociated from a tumor sample selected from the group consisting of gliomas, schwannomas, lung metastasis, brain metastasis, meningiomas and ependymomas.

* * * * *